(12) United States Patent
Nicholas

(10) Patent No.: US 10,508,720 B2
(45) Date of Patent: Dec. 17, 2019

(54) ADAPTER ASSEMBLY WITH PLANETARY GEAR DRIVE FOR INTERCONNECTING ELECTROMECHANICAL SURGICAL DEVICES AND SURGICAL LOADING UNITS, AND SURGICAL SYSTEMS THEREOF

(71) Applicant: Covidien LP, Mansfield, MA (US)

(72) Inventor: David Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 410 days.

(21) Appl. No.: 15/398,785

(22) Filed: Jan. 5, 2017

(65) Prior Publication Data

US 2017/0211667 A1 Jul. 27, 2017

Related U.S. Application Data

(60) Provisional application No. 62/281,275, filed on Jan. 21, 2016.

(51) Int. Cl.
*F16H 19/00* (2006.01)
*A61B 17/068* (2006.01)
(Continued)

(52) U.S. Cl.
CPC ....... *F16H 19/005* (2013.01); *A61B 17/0682* (2013.01); *A61B 17/07207* (2013.01); *A61B 34/71* (2016.02); *B25F 3/00* (2013.01); *F16H 57/038* (2013.01); *F16H 57/039* (2013.01); *A61B 2017/0046* (2013.01); *A61B 2017/00389* (2013.01); *A61B 2017/00398* (2013.01); *A61B 2017/00473* (2013.01); *A61B 2017/00477* (2013.01); *A61B 2017/2912* (2013.01); *A61B 2017/2927* (2013.01); *A61B 2017/2929* (2013.01); *A61B 2218/00* (2013.01)

(58) Field of Classification Search
CPC .... F16H 19/005; F16H 57/038; F16H 57/039; A61B 17/07207; A61B 34/71; A61B 2017/00398; A61B 2017/00477; A61B 2017/2912; A61B 2017/2927; A61B 2017/2929
See application file for complete search history.

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

CA 2451558 A1 1/2003
CN 1547454 A 11/2004
(Continued)

OTHER PUBLICATIONS

Extended European Search Report corresponding to counterpart Int'l Appln. No. EP 17152380.6 dated Jun. 19, 2017.

*Primary Examiner* — Hemant Desai
*Assistant Examiner* — Veronica Martin

(57) ABSTRACT

The present disclosure relates to adapter assemblies for use with and to electrically and mechanically interconnect electromechanical surgical devices and surgical loading units, and to surgical systems including handheld electromechanical surgical devices and adapter assemblies for connecting surgical loading units to the handheld electromechanical surgical devices.

19 Claims, 17 Drawing Sheets

(51) Int. Cl.
*F16H 57/038* (2012.01)
*F16H 57/039* (2012.01)
*A61B 17/072* (2006.01)
*B25F 3/00* (2006.01)
*A61B 34/00* (2016.01)
*A61B 17/00* (2006.01)
*A61B 17/29* (2006.01)

(56) References Cited

U.S. PATENT DOCUMENTS

| | | | |
|---|---|---|---|
| 3,111,328 A | 11/1963 | Di Rito et al. | |
| 3,695,058 A | 10/1972 | Keith, Jr. | |
| 3,734,515 A | 5/1973 | Dudek | |
| 3,759,336 A | 9/1973 | Marcovitz et al. | |
| 4,162,399 A | 7/1979 | Hudson | |
| 4,606,343 A | 8/1986 | Conta et al. | |
| 4,705,038 A | 11/1987 | Sjostrom et al. | |
| 4,722,685 A | 2/1988 | de Estrada et al. | |
| 4,823,807 A | 4/1989 | Russell et al. | |
| 4,874,181 A | 10/1989 | Hsu | |
| 5,129,118 A | 7/1992 | Walmesley | |
| 5,129,570 A | 7/1992 | Schulze et al. | |
| 5,152,744 A | 10/1992 | Krause et al. | |
| 5,301,061 A | 4/1994 | Nakada et al. | |
| 5,312,023 A | 5/1994 | Green et al. | |
| 5,326,013 A | 7/1994 | Green et al. | |
| 5,350,355 A | 9/1994 | Sklar | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,411,508 A | 5/1995 | Bessler et al. | |
| 5,413,267 A | 5/1995 | Solyntjes et al. | |
| 5,427,087 A | 6/1995 | Ito et al. | |
| 5,433,721 A | 7/1995 | Hooven et al. | |
| 5,467,911 A | 11/1995 | Tsuruta et al. | |
| 5,476,379 A | 12/1995 | Disel | |
| 5,487,499 A | 1/1996 | Sorrentino et al. | |
| 5,518,163 A | 5/1996 | Hooven | |
| 5,518,164 A | 5/1996 | Hooven | |
| 5,526,822 A | 6/1996 | Burbank et al. | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,540,375 A | 7/1996 | Bolanos et al. | |
| 5,540,706 A | 7/1996 | Aust et al. | |
| 5,542,594 A | 8/1996 | McKean et al. | |
| 5,549,637 A | 8/1996 | Crainich | |
| 5,553,675 A | 9/1996 | Pitzen et al. | |
| 5,562,239 A | 10/1996 | Boiarski et al. | |
| 5,564,615 A | 10/1996 | Bishop et al. | |
| 5,609,560 A | 3/1997 | Ichikawa et al. | |
| 5,626,587 A | 5/1997 | Bishop et al. | |
| 5,632,432 A | 5/1997 | Schulze et al. | |
| 5,645,209 A | 7/1997 | Green et al. | |
| 5,647,526 A | 7/1997 | Green et al. | |
| 5,653,374 A | 8/1997 | Young et al. | |
| 5,658,300 A | 8/1997 | Bito et al. | |
| 5,662,662 A | 9/1997 | Bishop et al. | |
| 5,667,517 A | 9/1997 | Hooven | |
| 5,693,042 A | 12/1997 | Boiarski et al. | |
| 5,704,534 A | 1/1998 | Huitema et al. | |
| 5,713,505 A | 2/1998 | Huitema | |
| 5,762,603 A | 6/1998 | Thompson | |
| 5,779,130 A | 7/1998 | Alesi et al. | |
| 5,782,396 A | 7/1998 | Mastri et al. | |
| 5,782,397 A | 7/1998 | Koukline | |
| 5,792,573 A | 8/1998 | Pitzen et al. | |
| 5,797,536 A | 8/1998 | Smith et al. | |
| 5,797,900 A | 8/1998 | Madhani et al. | |
| 5,820,009 A | 10/1998 | Melling et al. | |
| 5,863,159 A | 1/1999 | Lasko | |
| 5,908,427 A | 6/1999 | McKean et al. | |
| 5,954,259 A | 9/1999 | Viola et al. | |
| 5,964,774 A | 10/1999 | McKean et al. | |
| 5,993,454 A | 11/1999 | Longo | |
| 6,010,054 A | 1/2000 | Johnson et al. | |
| 6,017,354 A | 1/2000 | Culp et al. | |
| 6,032,849 A | 3/2000 | Mastri et al. | |
| 6,045,560 A | 4/2000 | McKean et al. | |
| 6,090,123 A | 7/2000 | Culp et al. | |
| 6,126,651 A | 10/2000 | Mayer | |
| 6,129,547 A | 10/2000 | Cise et al. | |
| 6,165,169 A | 12/2000 | Panescu et al. | |
| 6,239,732 B1 | 5/2001 | Cusey | |
| 6,241,139 B1 | 6/2001 | Milliman et al. | |
| 6,264,086 B1 | 7/2001 | McGuckin, Jr. | |
| 6,264,087 B1 | 7/2001 | Whitman | |
| 6,302,311 B1 | 10/2001 | Adams et al. | |
| 6,315,184 B1 | 11/2001 | Whitman | |
| 6,321,855 B1 | 11/2001 | Barnes | |
| 6,329,778 B1 | 12/2001 | Culp et al. | |
| 6,343,731 B1 | 2/2002 | Adams et al. | |
| 6,348,061 B1 | 2/2002 | Whitman | |
| 6,368,324 B1 | 4/2002 | Dinger et al. | |
| 6,371,909 B1 | 4/2002 | Hoeg et al. | |
| 6,434,507 B1 | 8/2002 | Clayton et al. | |
| 6,443,973 B1 | 9/2002 | Whitman | |
| 6,461,372 B1 | 10/2002 | Jensen et al. | |
| 6,488,197 B1 | 12/2002 | Whitman | |
| 6,491,201 B1 | 12/2002 | Whitman | |
| 6,533,157 B1 | 3/2003 | Whitman | |
| 6,537,280 B2 | 3/2003 | Dinger et al. | |
| 6,610,066 B2 | 8/2003 | Dinger et al. | |
| 6,611,793 B1 | 8/2003 | Burnside et al. | |
| 6,645,218 B1 | 11/2003 | Cassidy et al. | |
| 6,654,999 B2 | 12/2003 | Stoddard et al. | |
| 6,698,643 B2 | 3/2004 | Whitman | |
| 6,699,177 B1 | 3/2004 | Wang et al. | |
| 6,716,233 B1 | 4/2004 | Whitman | |
| 6,743,240 B2 | 6/2004 | Smith et al. | |
| 6,783,533 B2 | 8/2004 | Green et al. | |
| 6,792,390 B1 | 9/2004 | Burnside et al. | |
| 6,793,652 B1 | 9/2004 | Whitman et al. | |
| 6,817,508 B1 | 11/2004 | Racenet et al. | |
| 6,830,174 B2 | 12/2004 | Hillstead et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,860,892 B1 | 3/2005 | Tanaka et al. | |
| 6,899,538 B2 | 5/2005 | Matoba | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 6,986,451 B1 | 1/2006 | Mastri et al. | |
| 6,988,649 B2 | 1/2006 | Shelton, IV et al. | |
| 7,032,798 B2 | 4/2006 | Whitman et al. | |
| RE39,152 E | 6/2006 | Aust et al. | |
| 7,055,731 B2 | 6/2006 | Shelton, IV et al. | |
| 7,059,508 B2 | 6/2006 | Shelton, IV et al. | |
| 7,077,856 B2 | 7/2006 | Whitman | |
| 7,111,769 B2 | 9/2006 | Wales et al. | |
| 7,122,029 B2 | 10/2006 | Koop et al. | |
| 7,140,528 B2 | 11/2006 | Shelton, IV | |
| 7,141,049 B2 | 11/2006 | Stern et al. | |
| 7,143,923 B2 | 12/2006 | Shelton, IV et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,172,104 B2 | 2/2007 | Scirica et al. | |
| 7,225,964 B2 | 6/2007 | Mastri et al. | |
| 7,238,021 B1 | 7/2007 | Johnson | |
| 7,246,734 B2 | 7/2007 | Shelton, IV | |
| 7,252,660 B2 | 8/2007 | Kunz | |
| 7,328,828 B2 | 2/2008 | Ortiz et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,407,078 B2 | 8/2008 | Shelton, IV et al. | |
| 7,416,101 B2 | 8/2008 | Shelton, IV et al. | |

(56) References Cited

U.S. PATENT DOCUMENTS

| | | |
|---|---|---|
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,241,712 B2 | 1/2016 | Zemlok et al. |
| 9,272,406 B2 * | 3/2016 | Aronhalt ............ A61B 17/0682 |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,724,094 B2 * | 8/2017 | Baber .................. A61B 90/92 |
| 9,993,258 B2 * | 6/2018 | Shelton, IV ......... A61B 17/072 |
| 10,117,650 B2 * | 11/2018 | Nicholas ............. A61B 17/072 |
| 10,123,799 B2 * | 11/2018 | Zergiebel ......... A61B 17/07207 |
| 2001/0031975 A1 | 10/2001 | Whitman et al. |
| 2002/0049454 A1 | 4/2002 | Whitman et al. |
| 2002/0165541 A1 | 11/2002 | Whitman |
| 2003/0038938 A1 | 2/2003 | Jung et al. |

(56) References Cited

U.S. PATENT DOCUMENTS

| | | |
|---|---|---|
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0287977 A1* | 11/2008 | Viola ............ A61B 17/07207 606/171 |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1* | 8/2010 | Scheib ............ A61B 17/07207 227/176.1 |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2013/0093149 A1 | 4/2013 | Saur et al. |
| 2013/0098970 A1* | 4/2013 | Racenet ............ A61B 17/07207 227/180.1 |
| 2013/0112730 A1* | 5/2013 | Whitman ............ A61B 17/07207 227/175.1 |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0222019 A1 | 8/2014 | Brudniok |
| 2014/0236174 A1* | 8/2014 | Williams ............ A61B 17/00234 606/130 |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |

(56) References Cited

U.S. PATENT DOCUMENTS

| | | | |
|---|---|---|---|
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0000513 A1* | 1/2016 | Shelton, IV | A61B 17/07207 606/130 |
| 2016/0095585 A1 | 4/2016 | Zergiebel et al. | |
| 2016/0095596 A1 | 4/2016 | Scirica et al. | |
| 2016/0106406 A1* | 4/2016 | Cabrera | A61B 17/1155 606/1 |
| 2016/0113648 A1 | 4/2016 | Zergiebel et al. | |
| 2016/0113649 A1 | 4/2016 | Zergiebel et al. | |
| 2016/0324518 A1* | 11/2016 | Nicholas | A61B 17/072 |
| 2018/0125594 A1* | 5/2018 | Beardsley | A61B 34/71 |
| 2018/0344319 A1* | 12/2018 | Shelton, IV | A61B 17/320016 |

FOREIGN PATENT DOCUMENTS

| | | | |
|---|---|---|---|
| CN | 1957854 A | 5/2007 | |
| CN | 101495046 A | 7/2009 | |
| CN | 102247182 A | 11/2011 | |
| DE | 102008053842 A1 | 5/2010 | |
| EP | 0705571 A1 | 4/1996 | |
| EP | 1563793 A1 | 8/2005 | |
| EP | 1769754 A1 | 4/2007 | |
| EP | 2316345 A1 | 5/2011 | |
| EP | 2668910 A2 | 12/2013 | |
| EP | 2676615 A2 * | 12/2013 | ........... A61B 17/068 |
| EP | 2676615 A2 | 12/2013 | |
| ES | 2333509 A1 | 2/2010 | |
| JP | 2005-125075 A | 5/2005 | |
| KR | 20120022521 A | 3/2012 | |
| WO | 2009/039506 A1 | 3/2009 | |
| WO | 2011/108840 A2 | 9/2011 | |
| WO | 2012/040984 A1 | 4/2012 | |
| WO | 2012/068156 A2 | 5/2012 | |

* cited by examiner

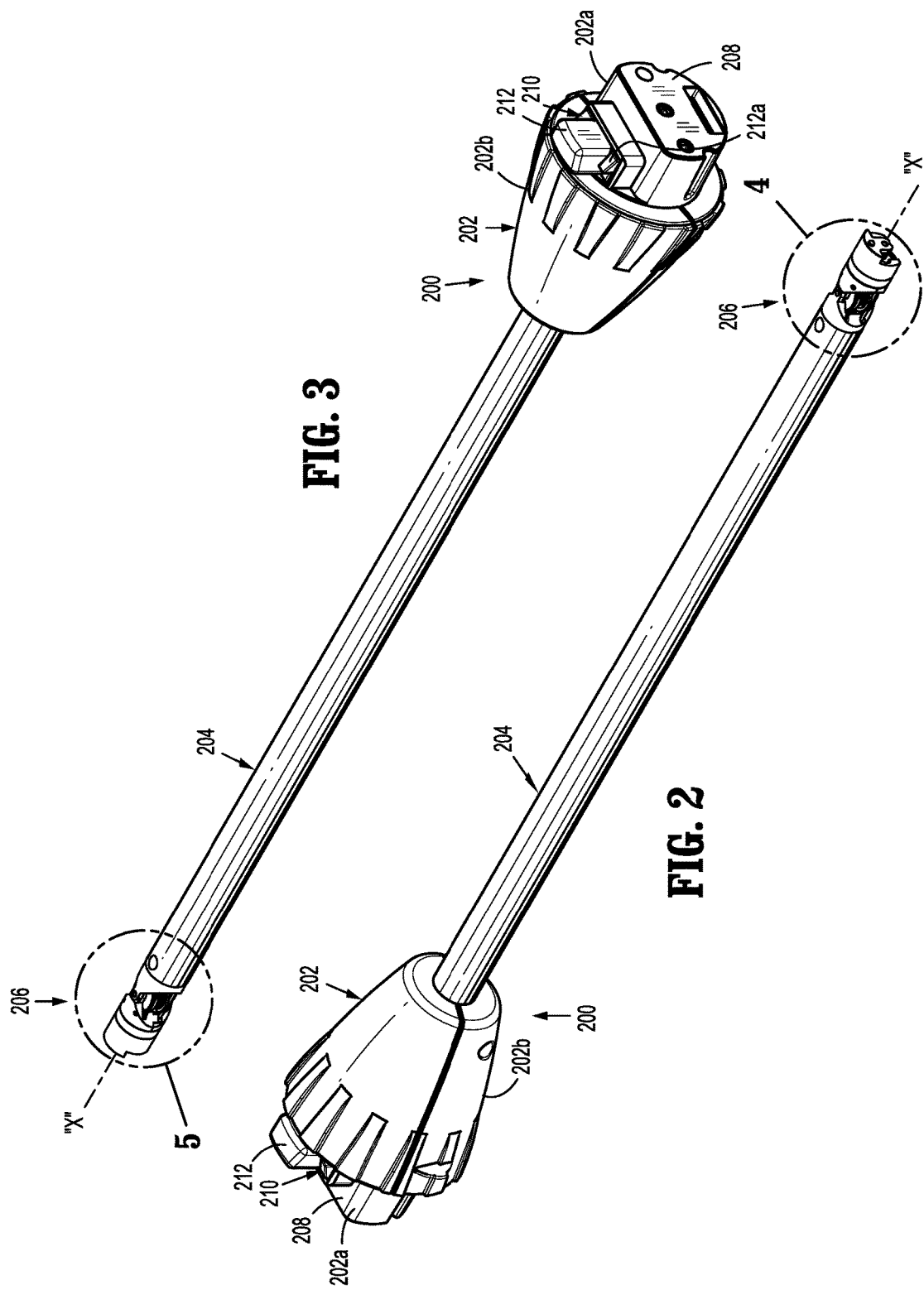

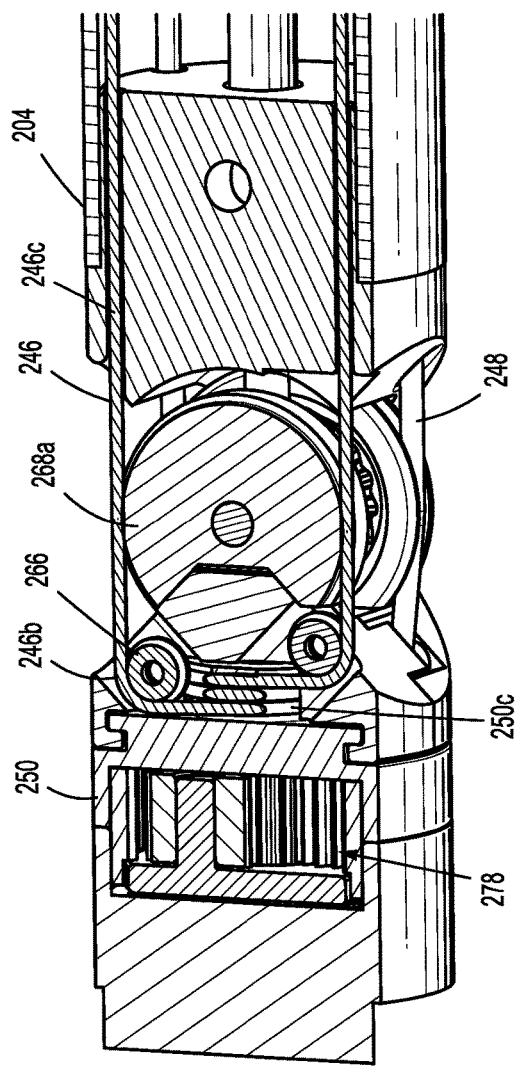
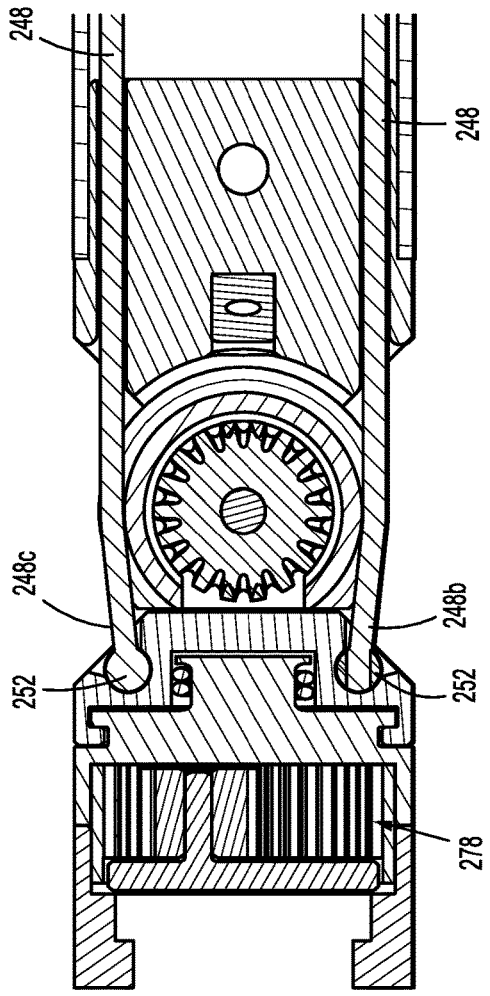
FIG. 14
FIG. 15

ADAPTER ASSEMBLY WITH PLANETARY GEAR DRIVE FOR INTERCONNECTING ELECTROMECHANICAL SURGICAL DEVICES AND SURGICAL LOADING UNITS, AND SURGICAL SYSTEMS THEREOF

CROSS-REFERENCE TO RELATED APPLICATIONS

This application claims the benefit of and priority to U.S. Provisional Patent Application No. 62/281,275 filed Jan. 21, 2016, the entire disclosure of which is incorporated by reference herein.

TECHNICAL FIELD

The present disclosure relates to adapter assemblies for use in surgical systems. More specifically, the present disclosure relates to adapter assemblies for use with, and to electrically and mechanically interconnect, electromechanical surgical devices and surgical loading units, and to surgical systems including handheld electromechanical surgical devices and adapter assemblies for connecting surgical loading units to the handheld electromechanical surgical devices.

BACKGROUND

A number of surgical device manufacturers have developed product lines with proprietary powered drive systems for operating and/or manipulating a surgical device. In many instances the surgical devices include a powered handle assembly, which is reusable, and a disposable end effector or the like that is selectively connected to the powered handle assembly prior to use and then disconnected from the end effector following use in order to be disposed of or in some instances, sterilized for re-use.

Many of the existing end effectors for use with many of the existing powered surgical devices and/or handle assemblies are driven by a linear force. For examples, end effectors for performing endo-gastrointestinal anastomosis procedures, end-to-end anastomosis procedures and transverse anastomosis procedures, each typically require a linear driving force in order to be operated. As such, these end effectors are not compatible with surgical devices and/or handle assemblies that use a rotary motion to deliver power or the like.

In order to make the linear driven end effectors compatible with powered surgical devices and/or handle assemblies that use a rotary motion to deliver power, adapters and/or adapter assemblies are used to interface between and interconnect the linear driven end effectors with the powered rotary driven surgical devices and/or handle assemblies. For example, in a motor powered stapling device, a lead screw/nut assembly is used to convert rotary motor torque to linear force. This linear force is used for clamping jaws of the stapling device and advancing a wedge to advance the staple pusher to form staples. In a motor powered articulating stapling device, it is desirable to place the lead screw in front of the articulation joint. Linear force, however, is difficult to pass through a bend (e.g., a 90° bend) in the articulation joint without significant losses and increased torque is needed through the articulation joint to perform the clamping and/or stapling operation.

Accordingly, a need exists for a powered rotary driven surgical device that requires less torque through an articulation joint to drive a linear driven end effector to minimize wear and to extend the usable life of the surgical device.

SUMMARY

According to an aspect of the present disclosure, an adapter assembly for selectively interconnecting a surgical loading unit that is configured to perform a function and a surgical device that is configured to actuate the surgical loading unit, the surgical loading unit including an axially translatable drive member, and the surgical device including a plurality of rotatable drive shafts, includes a housing, an outer tube, and a firing assembly. The housing is configured and adapted for connection with the surgical device. The outer tube extends distally from the housing to a distal end portion that is configured and adapted for connection with the surgical loading unit. The firing assembly is supported within the housing and outer tube and includes, from proximal to distal, a firing shaft, a bevel gear assembly, a ring gear, a sun gear, a plurality of planetary gears, a spider plate, and a distal gear. The firing shaft includes a proximal end configured for operative engagement with a rotatable drive shaft of the plurality of rotatable drive shafts of the surgical device. The bevel gear assembly includes a proximal end in mechanical engagement with a distal end portion of the firing shaft. The ring gear is disposed within the distal end portion of the outer tube, the sun gear is disposed at a distal end of the bevel gear assembly within the ring gear, and the plurality of planetary gears are disposed around and meshingly engaged with teeth of the sun gear and teeth of the ring gear. The spider plate is operably coupled to the plurality of planetary gears and the distal gear is disposed on a shaft extending distally from the spider plate. The distal gear is operatively engageable with the axially translatable drive member of the surgical loading unit.

In embodiments, the distal end portion of the outer tube includes an articulation joint. In some embodiments, the bevel gear assembly is disposed proximal of the articulation joint. In certain embodiments, the sun gear and the plurality of planetary gears are disposed distal of the articulation joint.

The bevel gear assembly may include a proximal bevel gear including a stem extending proximally therefrom that is operably coupled to a distal end portion of the firing shaft by a bearing. The bevel gear assembly may further includes a central bevel gear engaged with the proximal bevel gear. The bevel gear assembly may further includes a distal bevel gear engaged with the central bevel gear. In some embodiments, the distal bevel gear of the bevel gear assembly includes a stem extending distally therefrom, and the sun gear is secured to the stem of the distal bevel gear.

The spider plate may includes a proximal surface including a plurality of pegs extending proximally therefrom that may be disposed in openings defined in the plurality of planetary gears.

The adapter assembly may further include an articulation assembly including a worm gear assembly, a rotation cable, and an articulation cable. The worm gear assembly may include a first worm drive and a second worm drive disposed within the housing. The rotation cable may be operably connected to and extend distally from the first worm drive of the worm gear assembly through the outer tube to the ring gear which is disposed distal to the articulation joint such that rotation of the first worm drive results in rotation of the distal end portion of the outer tube. The articulation cable may be operably connected to and extend distally from the second worm drive of the worm gear assembly to retaining members disposed within the outer tube distal to the articulation joint such that rotation of the second worm drive results in articulation of the distal end portion of the outer tube about the articulation joint.

Each of the first and second worm drives may include a worm screw meshingly engaged with a worm wheel, with each worm screw configured to be in operative communication with a rotatable drive shaft of the plurality of drive shafts of the surgical device.

In some embodiments, the rotation cable includes a proximal end wound around a drum portion of the worm wheel of the first worm drive and a distal end wound around a drum of the ring gear. In some embodiments, the articulation cable includes a proximal end wound around a drum portion of the worm wheel of the second worm drive and distal ends coupled to respective retaining members. The articulation cable may include springs disposed between the proximal and distal ends of the articulation cable.

The articulation assembly may further include a first cable guide wheel and a second cable guide wheel for guiding the rotation and articulation cables, respectively. In some embodiments, the first and second cable guide wheels are circular in shape, and in some embodiments, the first and second cable guide wheels are cam-shaped.

In embodiments, the firing assembly further includes a spider gear operably coupled to the spider plate and disposed proximal of the ring gear, and the distal end portion of the outer tube includes a switch having a tab extending distally from a distal end of the switch and an extension extending inwardly toward a center of the outer tube. The switch is movable between a proximal position in which the tab is disengaged from the ring gear and the extension is engaged with the spider gear such that the spider plate is held stationary to allow the plurality of planetary gears to rotate the distal end portion of the outer tube, and a distal position in which the tab is engaged with the ring gear and the extension is disengaged from the spider gear such that the ring gear is held stationary to allow the plurality of planetary gears to effect a function of the surgical loading unit.

The adapter assembly may further includes an articulation assembly including a worm gear assembly, a pull cable, and an articulation cable. The worm gear assembly may include a first worm drive and a second worm drive disposed within the housing. The pull cable may be operably connected to and extend distally from the first worm drive of the worm gear assembly and into the outer tube, and may be configured to move the switch between the proximal and distal positions. The articulation cable may be operably connected to and extends distally from the worm gear assembly to retaining members disposed within the outer tube distal of the articulation joint such that rotation of the second worm drive results in articulation of the distal end portion of the outer tube about the articulation joint.

The articulation assembly may further include a first cable guide wheel including a cam, and the pull cable may include a proximal end wound around a drum portion of the worm wheel of the first worm drive of the worm gear assembly and a distal end wrapped around the first cable guide wheel such that rotation of the first worm drive results in movement of the cam against a camming surface of the switch to move the switch between the proximal and distal positions.

Embodiments can include one or more of the following advantages. In embodiments, adapter assemblies of the present disclosure include a planetary gear assembly placed on a distal side of an articulation joint to minimize the torque required through the articulation joint. By placing a planetary gear assembly distal to the articulation joint, the amount of torque the bevel gears need to transfer is reduced by approximately 75-80% due to the gear ratio provided by the planetary gears. The lower torque requirement on the bevel gears may extend the usable life of the adapter assembly and minimize wear. In embodiments, the planetary gear assembly is balanced and has multiple gears in mesh at all times, placing less stress on the gear teeth and bearings.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 2 is a perspective view of an adapter assembly of the electromechanical surgical system of FIG. 1;

FIG. 3 is another perspective view of the adapter assembly of FIGS. 1 and 2;

FIG. 14 is a cross-sectional view of the adapter assembly of FIGS. 1-6, taken along line 14-14 of FIG. 6;

FIG. 15 is a cross-sectional view of the adapter assembly of FIGS. 1-6, taken along line 15-15 of FIG. 6;

DETAILED DESCRIPTION

Figure 1:
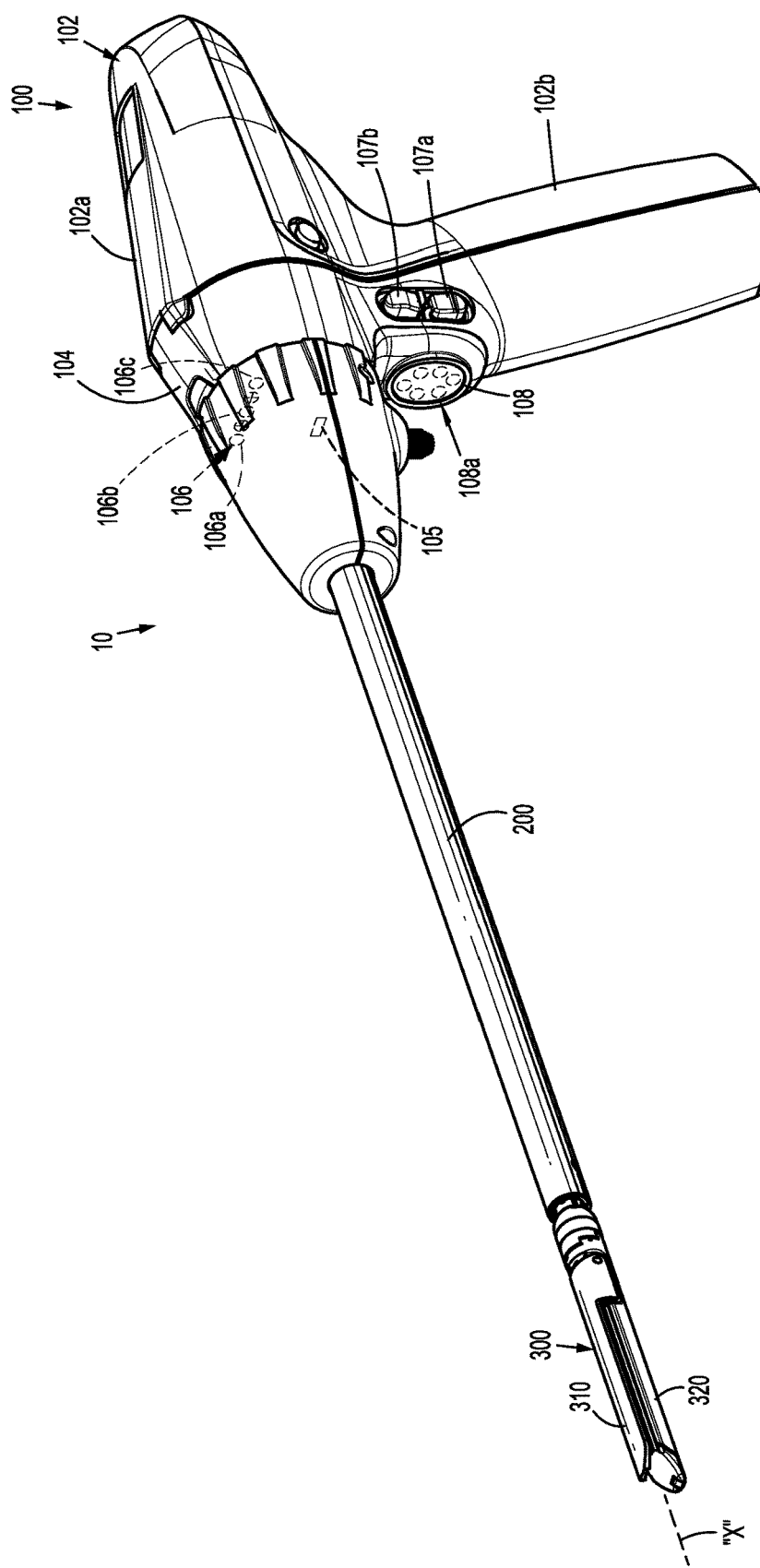
FIG. 1 is a perspective view of an electromechanical surgical system in accordance with the principles of the present disclosure.

Electromechanical surgical systems of the present disclosure include surgical devices in the form of powered handheld electromechanical instruments configured for selective attachment to a plurality of different end effectors that are each configured for actuation and manipulation by the powered handheld electromechanical surgical instrument. In particular, the presently described electromechanical surgical systems include adapter assemblies that interconnect the powered handheld electromechanical surgical instruments to the plurality of different end effectors. Each adapter assembly includes an articulation assembly and a firing assembly that is operatively coupled to a powered handheld electromechanical surgical instrument for effectuating actuation and/or manipulation of the plurality of different end effectors.

Embodiments of the presently disclosed electromechanical surgical systems, surgical devices/handle assemblies, adapter assemblies, and/or loading units are described in detail with reference to the drawings, in which like reference numerals designate identical or corresponding elements in each of the several views. As used herein the term "distal" refers to that portion of the system, assembly, device, and/or component thereof, farther from the user, while the term "proximal" refers to that portion of the system, assembly, device, and/or component thereof, closer to the user.

Turning now to FIG. 1, an electromechanical surgical system, in accordance with the present disclosure, generally referred to as 10, includes a surgical device 100 in the form of a powered handheld electromechanical instrument, an adapter assembly 200, and a surgical loading unit 300 (e.g., an end effector, multiple- or single-use loading unit). Surgical device 100 is configured for selective connection with adapter assembly 200, and, in turn, adapter assembly 200 is configured for selective connection with loading unit 300. Together, surgical device 100 and adapter assembly 200 may cooperate to actuate loading unit 300.

Surgical device 100 includes a handle housing 102 including a circuit board (not shown) and a drive mechanism (not shown) situated therein. The circuit board is configured to control the various operations of surgical device 100. Handle housing 102 defines a cavity therein (not shown) for selective removable receipt of a rechargeable battery (not shown) therein. The battery is configured to supply power to any of the electrical components of surgical device 100.

Handle housing 102 includes an upper housing portion 102a which houses various components of surgical device 100, and a lower hand grip portion 102b extending from upper housing portion 102a. Lower hand grip portion 102b may be disposed distally of a proximal-most end of upper housing portion 102a. The location of lower housing portion 102b relative to upper housing portion 102a is selected to balance a weight of a surgical device 100 that is connected to or supporting adapter assembly 200 and/or loading unit 300.

Handle housing 102 provides a housing in which the drive mechanism (not shown) is situated. The drive mechanism is configured to drive shafts and/or gear components in order to perform the various operations of surgical device 100. In particular, the drive mechanism is configured to drive shafts and/or gear components in order to selectively articulate loading unit 300 about a longitudinal axis "X" and relative to a distal end of adapter assembly 200, to selectively rotate loading unit 300 about longitudinal axis "X" and relative to handle housing 102, to selectively move/approximate/separate an anvil assembly 310 and a cartridge assembly 320 of loading unit 300 relative to one another, and/or to fire a stapling and cutting cartridge within cartridge assembly 320 of loading unit 300.

Handle housing 102 defines a connection portion 104 configured to accept a proximal end of adapter assembly 200. Connection portion 104 houses an articulation contact surface 105 in electrical communication with the circuit board (not shown) and a plurality of rotatable drive shafts or connectors 106. Each rotatable drive shaft of the plurality of rotatable drive shafts can be independently, and/or dependently, actuatable and rotatable by the drive mechanism (not shown) housed within housing handle 102. In embodiments, the plurality of rotatable drive shafts 106 includes rotatable drive shafts, 106a, 106b, and 106c arranged in a common plane or line with one another. As can be appreciated, the plurality of rotatable drive shafts can be arranged in any suitable configuration. The drive mechanism (not shown) may be configured to selectively drive one or more of the rotatable drive shafts 106 of surgical instrument 100, at a given time.

Handle housing 102 supports a plurality of finger-actuated control buttons, rocker devices, and the like for activating various functions of surgical device 100. For example, handle housing 102 supports a plurality of actuators including, for example, an actuation pad 108 in operative registration with a plurality of sensors 108a that cooperate with actuation pad 108 to effectuate, for example, opening, closing, and/or firing of loading unit 300. Handle housing 102 can support actuators 107a, 107b which can be disposed in electrical communication with the motors of handle housing 102 to effectuate rotation of rotatable drive shafts 106a, 106b, and/or 106c for actuation thereof to enable adjustment of one or more of the components of adapter assembly 200. Any of the presently described actuators can have any suitable configuration (e.g., button, knob, toggle, slide, etc.).

Reference may be made to International Application No. PCT/US2008/077249, filed Sep. 22, 2008 (Inter. Pub. No. WO 2009/039506), and U.S. Patent Application Publication No. 2011/0121049, filed on Nov. 20, 2009, the entire contents of each of which being incorporated herein by reference, for a detailed description of various internal components of and operation of exemplary electromechanical surgical systems, the components of which are combinable and/or interchangeable with one or more components of electromechanical surgical systems 10 described herein.

With reference to FIGS. 2-3, adapter assembly 200 includes a housing 202 at a proximal end portion thereof and an outer tube 204 that extends distally from housing 202 to a distal end portion 206 thereof along a longitudinal axis "X". Housing 202 of adapter assembly 200 includes a proximal housing 202a and a distal housing 202b. Proximal housing 202a includes a housing body 208 supporting a mounting assembly 210 thereon. Mounting assembly 210 includes a mounting button 212 that is biased in an extended position and is configured to be depressed downwardly to a compressed position. In the compressed position, mounting button 212 is disposed in close approximation with housing body 208 and offset from the extended position. Mounting button 212 includes sloped engagement features 212a that are configured to contact connection portion 104 (FIG. 1) of handle housing 102 while mounting button 212 is in the extended position to facilitate securement of housing 202 to connection portion 104 of handle housing 102.

As seen in FIGS. 4-7, distal end portion 206 of outer tube 204 includes a first segment 206a, a second segment 260b distal of first segment 206a, a third segment 260c distal of second segment 206b, and a fourth segment 206d distal of third segment 206c.

First segment 206a of distal end portion 206 of outer tube 204 defines a pair of screw openings 214 that correspond with a pair of screw openings 216 of second segment 206b. The pair of screw openings 214 of first segment 206a and the pair of screw openings 216 of second segment 206b receive a pair of screws 215 to fixedly secure first and second segments 206a and 206b together.

Second segment 206b includes a tapered distal end 218 having a pair of opposed openings 218a, and third segment 206c includes a tapered proximal end 220 having a pair of opposed openings 220a that are aligned with the pair of opposed openings 218a of second segment 206b. The pair of opposed openings 218a of second segment 206b and the pair of opposed openings 220a of third segment 206 receive a rod or pin 222 therethrough to pivotably secure second and third segments 206b and 206c together at an articulation joint 224. Third segment 206c may articulate relative to the second segment 206b about a transverse axis "Y" defined by rod 222 to move third segment 206c relative to longitudinal axis "X."

Third segment 206c includes a distal end 226 having a cylindrical lip 226a that mounts over a flanged proximal end 250a of a ring gear 250 that is fixedly secured at a distal end 250b thereof to a proximal end 228 of fourth segment 206d.

Fourth segment 206d includes a pair of arms 230a and 230b at a distal end 232 of fourth segment 206d and that are disposed in spaced apart and mirrored relation to one another. Fourth segment 206d includes a plunger assembly 234 that includes a plunger 234a that is biased through a plunger opening 234b by a spring 234c. Plunger assembly 234 and the pair of arms 230a and 230b cooperate to facilitate securement of a proximal end of loading unit 300 to distal end portion 206 of outer tube 204 of adapter assembly 200 as described in greater detail below. A tongue 236 depends from fourth segment 206d and defines an opening 236a therethrough as also described in greater detail below.

With reference now to FIGS. 7-16, an articulation assembly 240 is supported within housing 202 and outer tube 204. Articulation assembly 240 includes input sockets 242a and 242c (FIG. 8) adapted to couple to rotatable drive shafts 106a and 106c, respectively, of handle housing 102 (FIG. 1), a worm gear assembly 244 disposed within housing 202 that is operably connected to and extends distally from input sockets 242a and 242c, a rotation cable 246 operably connected to and extending distally from worm gear assembly 244 through outer tube 204 to ring gear 250, and an articulation cable 248 operably connected to and extending distally from worm gear assembly 244 through outer tube 204 to retaining members 252 secured within third segment 206c of distal end 206 of outer tube 204.

Figure 8:
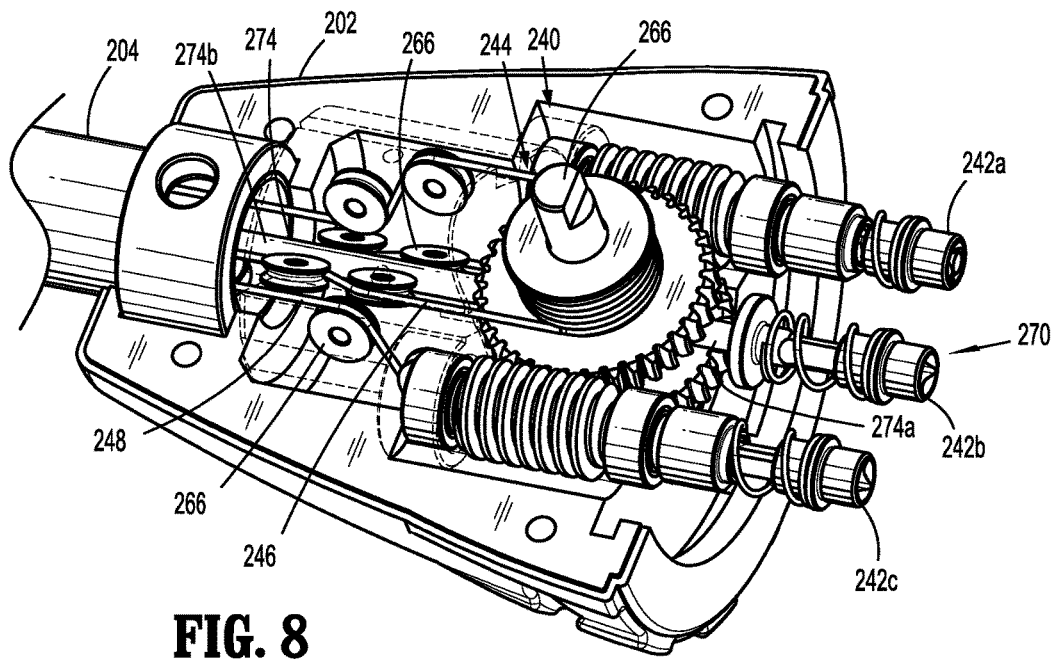
FIG. 8 is a top perspective view, with parts removed, of internal components of a housing of the adapter assembly of FIGS. 1-3.
Figure 9:
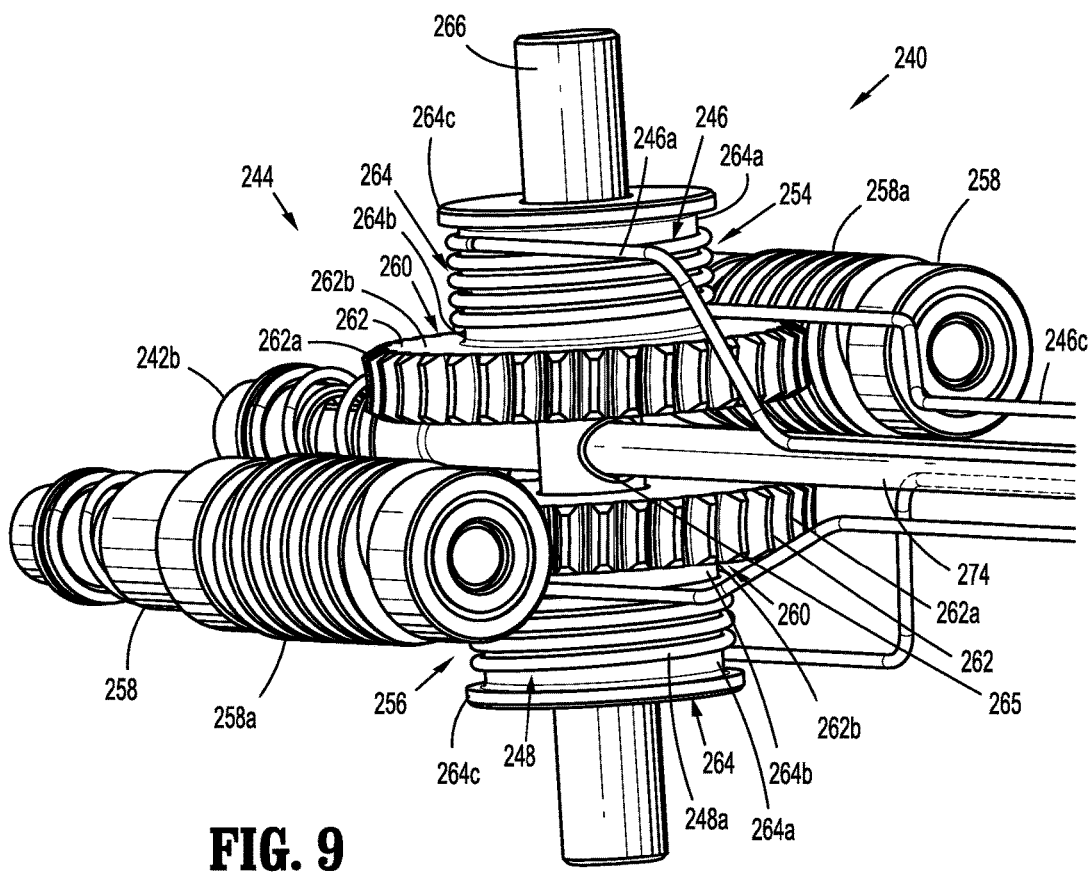
FIG. 9 is an enlarged, perspective view of a worm gear assembly disposed within the housing of the adapter assembly of FIG. 8.
Figure 10:
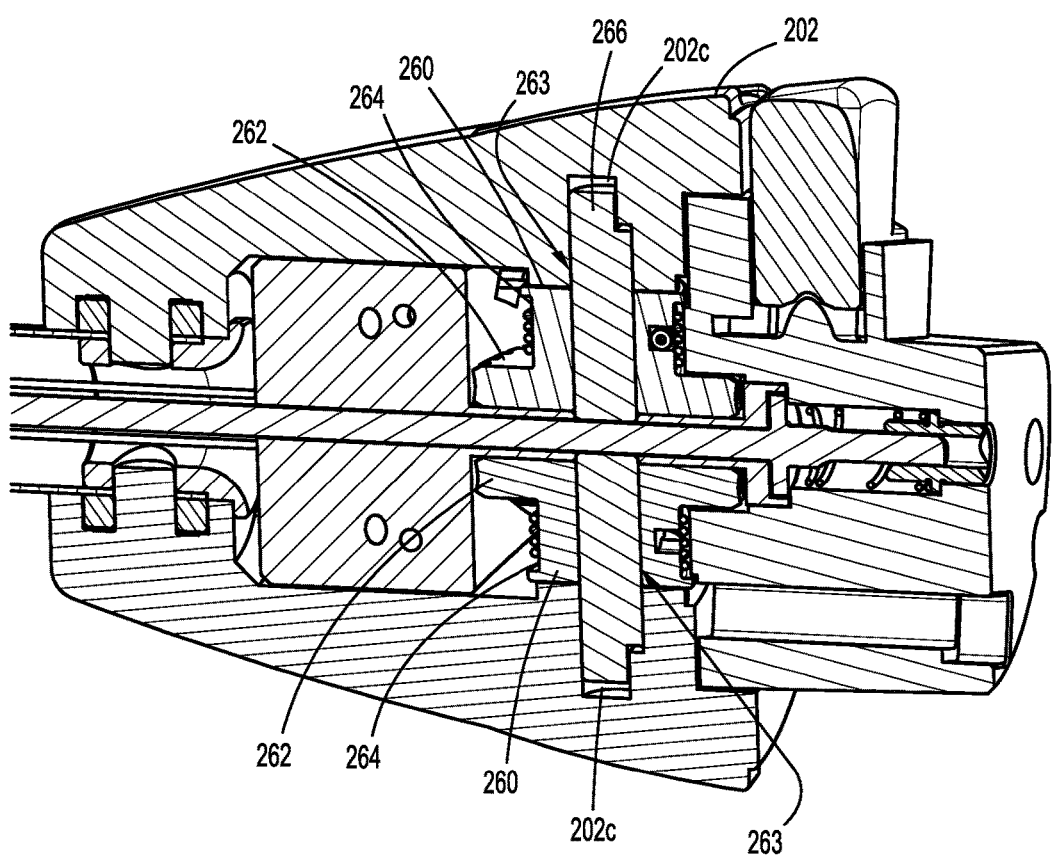
FIG. 10 is side, cross-sectional view of the housing of the adapter assembly of FIGS. 1-3 and 8.

As shown in FIGS. 8-10, worm gear assembly 244 includes a first worm drive 254 and a second worm drive 256. First and second worm drives 254 and 256 each include a worm screw or gear 258 and a worm wheel or spur gear 260. Each worm screw 258 includes a threaded body 258a that extends distally from a respective input socket 242a or 242c, with a distal end of input socket 242a and 242c mechanically coupled to a proximal end of the respective worm screw 258. Each worm wheel 260 includes a gear portion 262 and a drum portion 264, and defines a central opening 263 extending through the gear and drum portions 262 and 264. In embodiments, the gear and drum portions 262 and 264 are concentric with each other about central opening 263. Central opening 263 is configured to receive a support shaft 266 which is securely retained within recesses 202c defined in housing 202 to facilitate securement of each worm wheel 260 to housing 202. Gear portion 262 of worm wheel 260 includes a plurality of teeth 262a on an external surface thereof which are configured and dimensioned to meshingly engage threaded body 258a of worm screw 258. Drum portion 264 includes a cylindrical drum surface 264a having at first end portion 264b terminating at a side surface 262b of gear portion 262 and a flanged second end portion 264c such that first and second end portions 264b and 264c have a larger diameter than that of drum surface 264a for retaining the respective rotation or articulation cable 246 or 248 on drum surface 264a.

As shown, for example, in FIGS. 7-9, 14, and 16, rotation cable 246 includes a proximal end portion 246a wound around drum surface 264a of drum portion 264 of worm wheel 260 of the first worm drive 254, and a distal end portion 246b wound around a proximal drum 250c of ring gear 250. A central portion 246c of rotation cable 246 extends between proximal and distal end portions 246a and 246b, and is guided by a plurality of rollers 266 and a first cable guide wheel 268a through outer tube 204.

In use, rotation of rotatable drive shaft 106c (e.g., clockwise or counterclockwise) of surgical device 100 causes a corresponding rotation of input socket 242c and thus worm screw 258 of first worm drive 254 of adapter assembly 200, which in turn, rotates worm wheel 260 of first worm drive 254 in a corresponding direction about a "Y" axis defined by support shaft 266. Rotation of worm wheel 260 moves/slides rotation cable 246 in a corresponding direction which pulls and rotates ring gear 250 about the longitudinal axis "X." As distal end 250b of ring gear 250 is fixedly attached to fourth segment 206d of distal end portion 206, rotation of ring gear 250 causes a corresponding rotation of fourth segment 206d of distal end portion 206 of outer tube 204 about longitudinal axis "X."

As shown, for example, in FIGS. 7-9, 11, 12, 15, and 16, articulation cable 248 includes a proximal end 248a wound around drum surface 264a of drum portion 264 of worm wheel 260 of second worm drive 256, and distal ends 248b and 248c coupled to retaining members 252 fixed within recesses 207 defined in third segment 206c of distal end portion 206 of outer tube 204 to secure distal ends 248b and 248c of articulation cable 248 to distal end portion 206 of outer tube 204. A central portion 248d of articulation cable 248 is guided by a plurality of rollers 266 and a second cable guide wheel 268b. Central portion 248d also includes springs 249 to compensate for changes in the tension/slack of articulation cable 248 during use.

In use, rotation of rotatable drive shaft 106a (e.g., clockwise or counterclockwise) of surgical device 100 causes a corresponding rotation of input socket 242a and thus worm screw 258 of second worm drive 256 of adapter assembly 200, which in turn, rotates worm wheel 260 of second worm drive 256 in a corresponding direction about support shaft 266. Rotation of worm wheel 260 draws/retracts/tightens one side of articulation cable 248 and lets out/releases the other side of articulation cable 248. As retaining members 262 are disposed within third segment 206c, tension/slack on articulation cable 248 causes articulation of third segment 206c and thus fourth segment 206d of distal end portion 206 of outer tube 204 relative to longitudinal axis "X" about articulation joint 224.

With reference now to FIGS. 7-19, a firing assembly 270 is supported within housing 202 and outer tube 204 of adapter assembly 200. Firing assembly 270 includes an input socket 272b adapted to couple to rotatable drive shaft 106b of housing handle 102 (see FIG. 1), a firing shaft 274 extending distally from input socket 272, a bevel gear assembly 276 extending distally from and in mechanical engagement with firing shaft 274, a plurality of planetary gears 278 disposed around a portion of bevel gear assembly 276, a spider plate 280 operably coupled to the plurality of planetary gears 278, and a distal gear 282 disposed on a distal end of spider plate 280.

Firing shaft 274 includes a proximal end portion 274a that is received in, and mechanically coupled to, a distal end of input socket 272, a body portion 274b extending distally from proximal end portion 274a, and a distal end portion 274c having a tapered shape that extends distally from body portion 274b. Proximal end portion 274a of firing shaft 274 is supported within housing 202, and extends distally through an opening 265 defined within support shaft 266 between first and second worm drives 254 and 256. Distal end portion 274c of firing shaft 274 is disposed within a bearing 284.

As shown, for example, in FIGS. 7, 12, 13, and 17-19, bevel gear assembly 276 includes a proximal bevel gear 286, a central bevel gear 288, and a distal bevel gear 290 that are sequentially engaged with each other. Proximal bevel gear 286 includes a stem 286a extending proximally therefrom that is operably connected to distal end portion 274c of firing shaft 274 by bearing 284 for rotation with firing shaft 274 about longitudinal axis "X." Proximal bevel gear 286 has a plurality of teeth 286b formed along a distal end thereof that are in meshing engagement with teeth 288a of a central bevel gear 288 such that rotation of proximal bevel gear 286 results in rotation of central bevel gear 288 about an axis of rotation transverse to longitudinal axis "X." Teeth 288a of central bevel gear 288 are also meshingly engaged with teeth 290a of a distal bevel gear 290 such that rotation of central bevel gear 288 results in rotation of distal bevel gear 290 about longitudinal axis "X." Distal bevel gear 290 includes a stem 290b extending distally therefrom. A sun gear 292 is disposed at a distal end of stem 290b of distal bevel gear 290 within ring gear 250 such that rotation of distal bevel gear 290 results in rotation of sun gear 292 about longitudinal axis "X." The plurality of planetary gears 278 are disposed around and meshingly engaged with teeth 292a of sun gear 292 and with teeth 250d disposed within an inner surface of ring gear 250 such that rotation of sun gear 292 results in rotation of the plurality of planetary gears 278 within ring gear 250.

Spider plate 280 includes a proximal surface 280a affixed to the plurality of planetary gears 278 such that rotation of the plurality of planetary gears 278 within ring gear 250 results in rotation of spider plate 280. In embodiments, spider plate 280 includes a plurality of pegs 280b that are press fit into openings 278a defined in the plurality of planetary gears 278. Spider plate 280 includes a shaft 280c extending distally therefrom on which distal gear 282 is non-rotatably disposed such that rotation of spider plate 280 causes a corresponding rotation of distal gear 282 about longitudinal axis "X."

Figure 4:
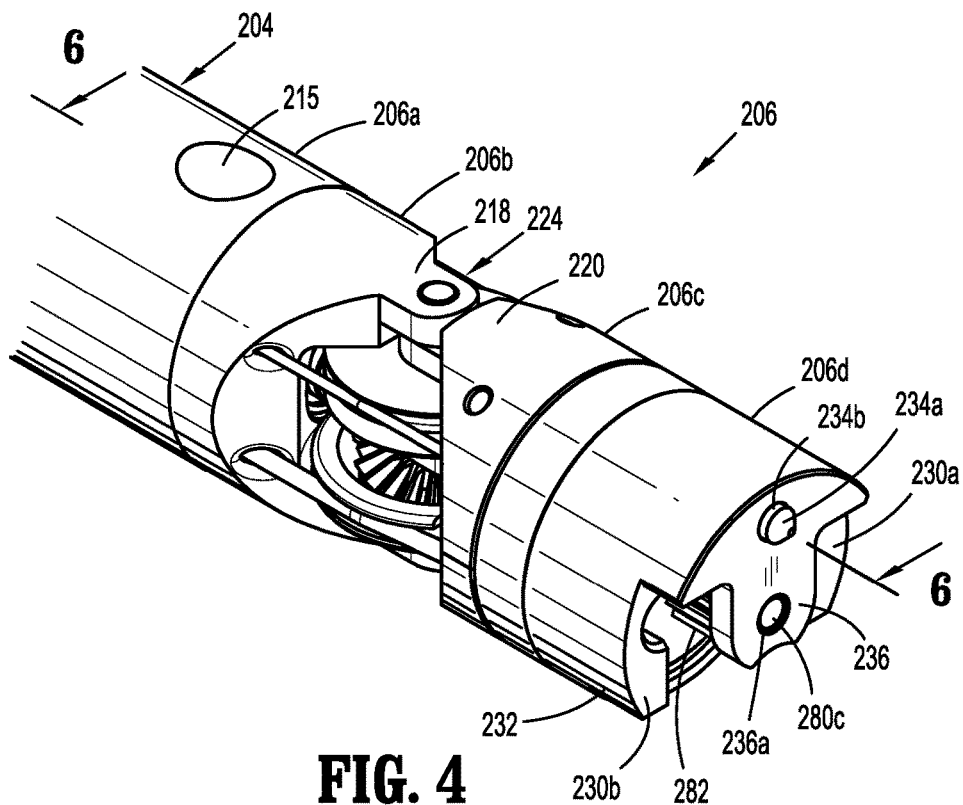
FIG. 4 is an enlarged, perspective view of the indicated area of detail shown in FIG. 2.
Figure 5:
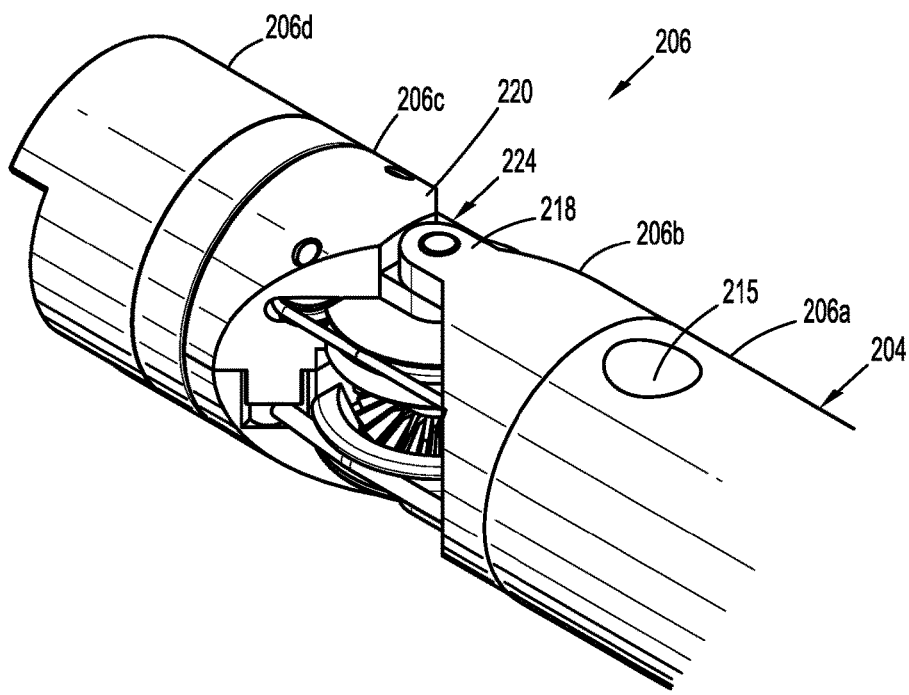
FIG. 5 is an enlarged, perspective view of the indicated area of detail shown in FIG. 3.
Figure 6:
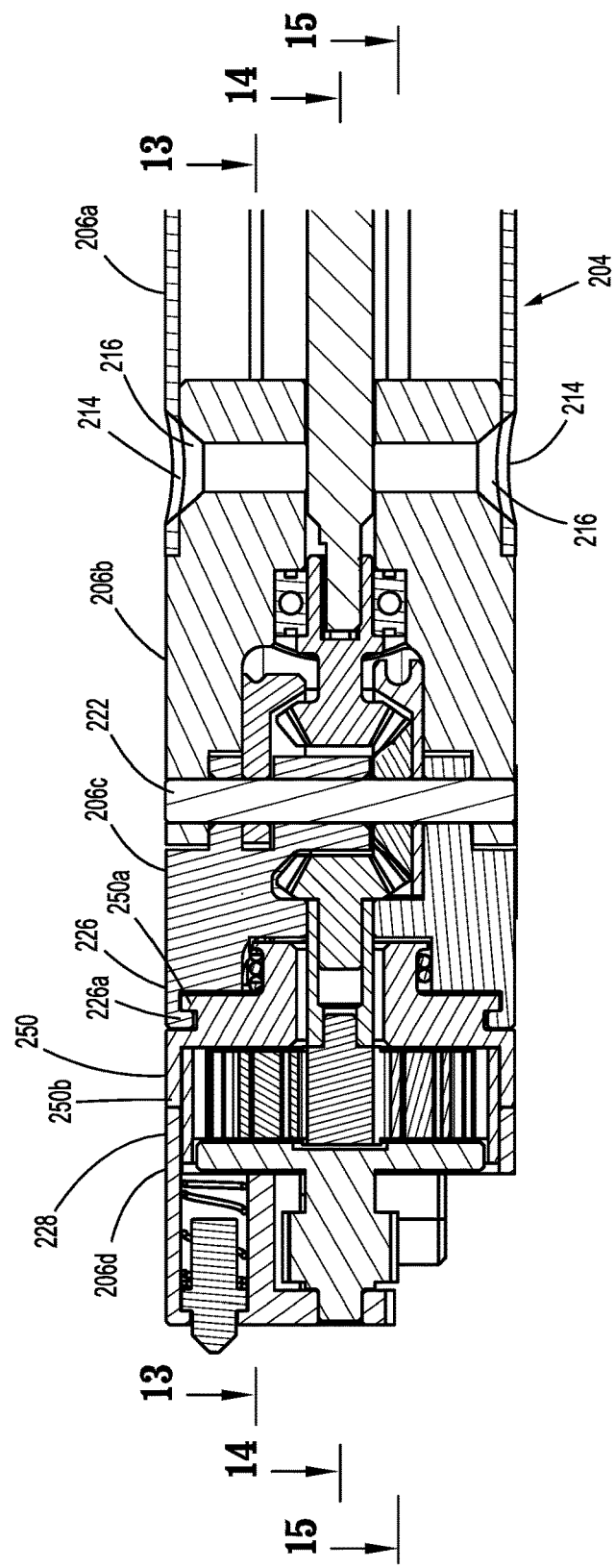
FIG. 6 is a cross-sectional view of a distal end portion of the adapter assembly of FIGS. 1-4, taken along line 6-6 of FIG. 4.
Figure 7:
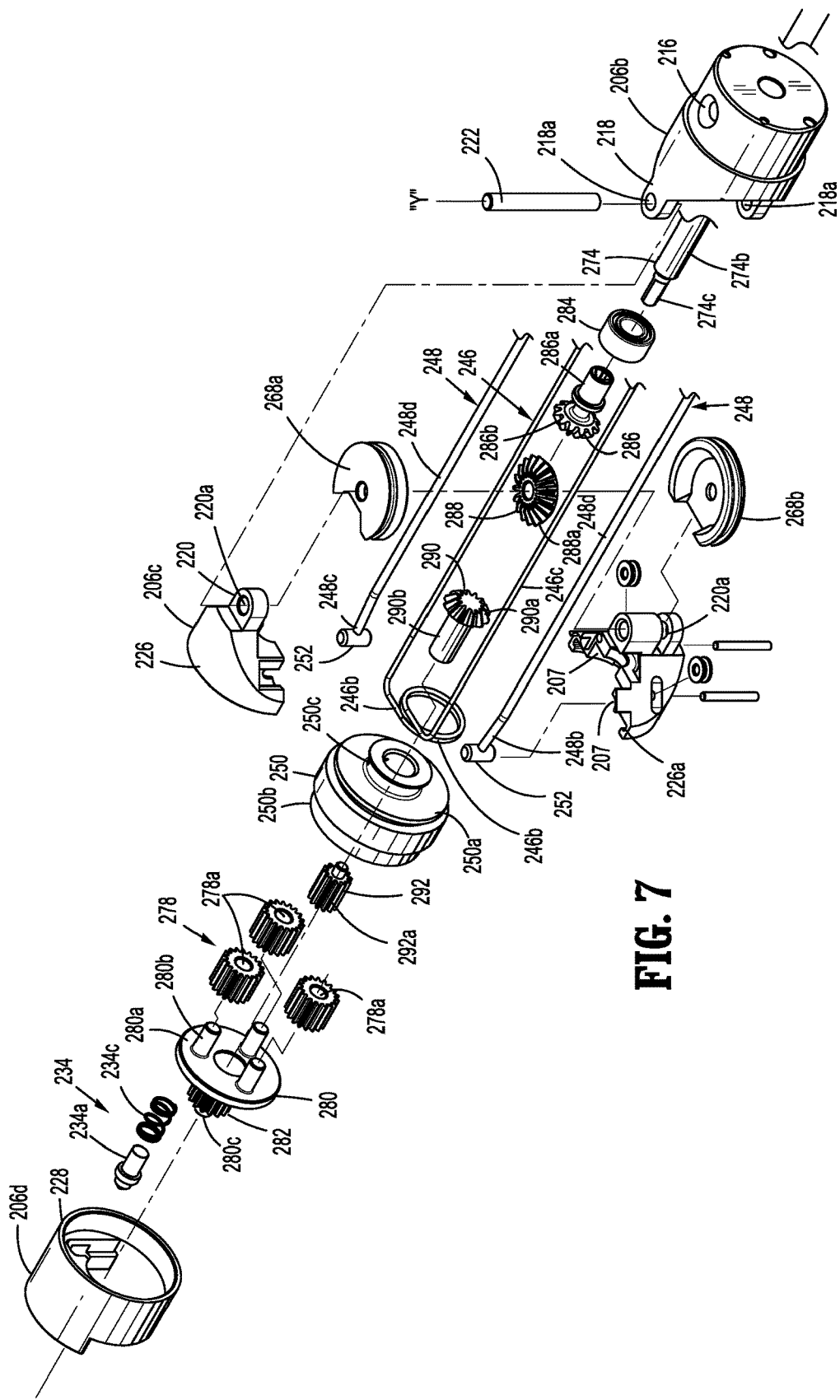
FIG. 7 is a perspective view, with parts separated, of the distal end portion of the adapter assembly of FIGS. 1-6.
Figure 12:
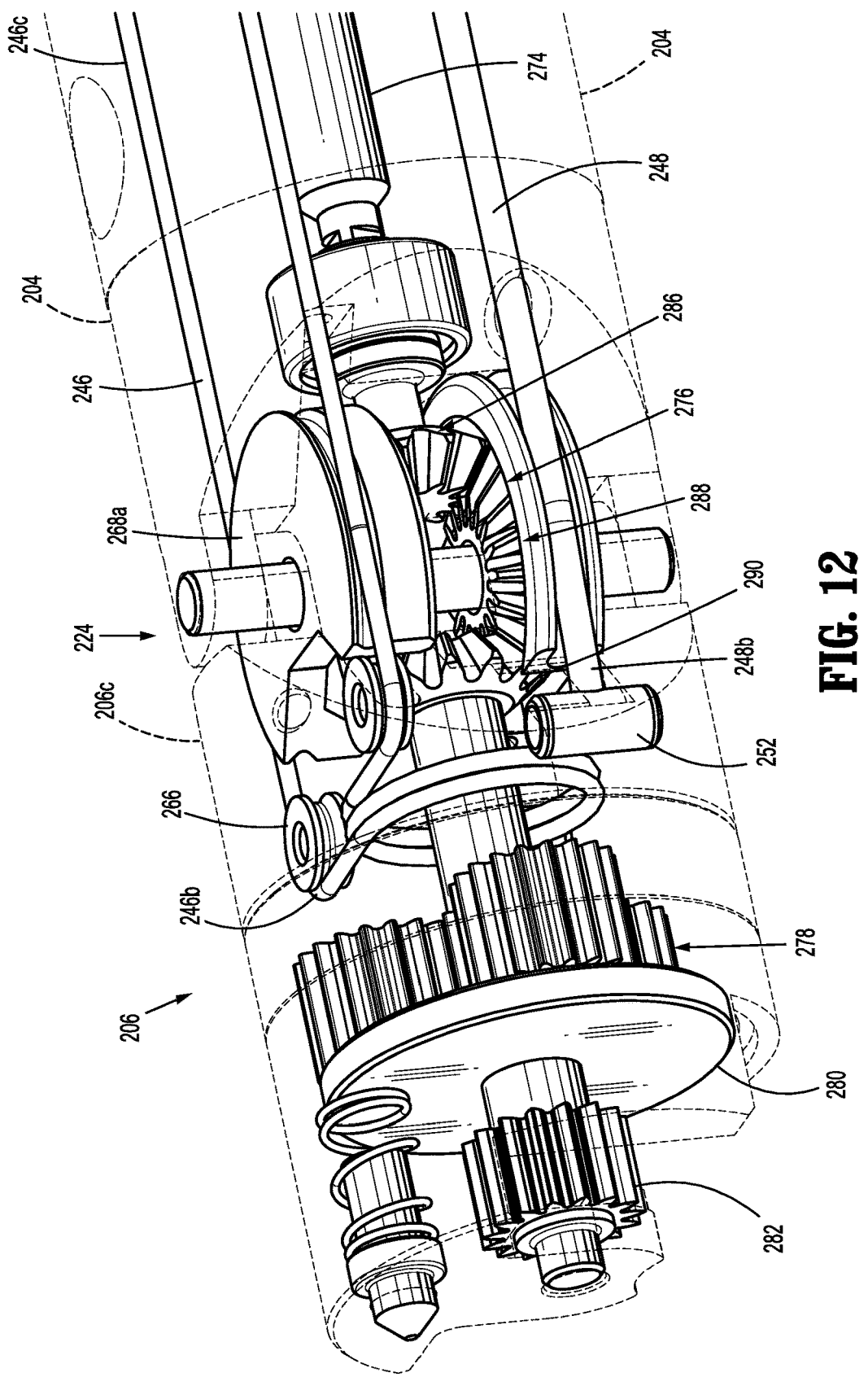
FIG. 12 is an enlarged, perspective view of the distal end portion of the adapter assembly of FIGS. 1-7.
Figure 13:
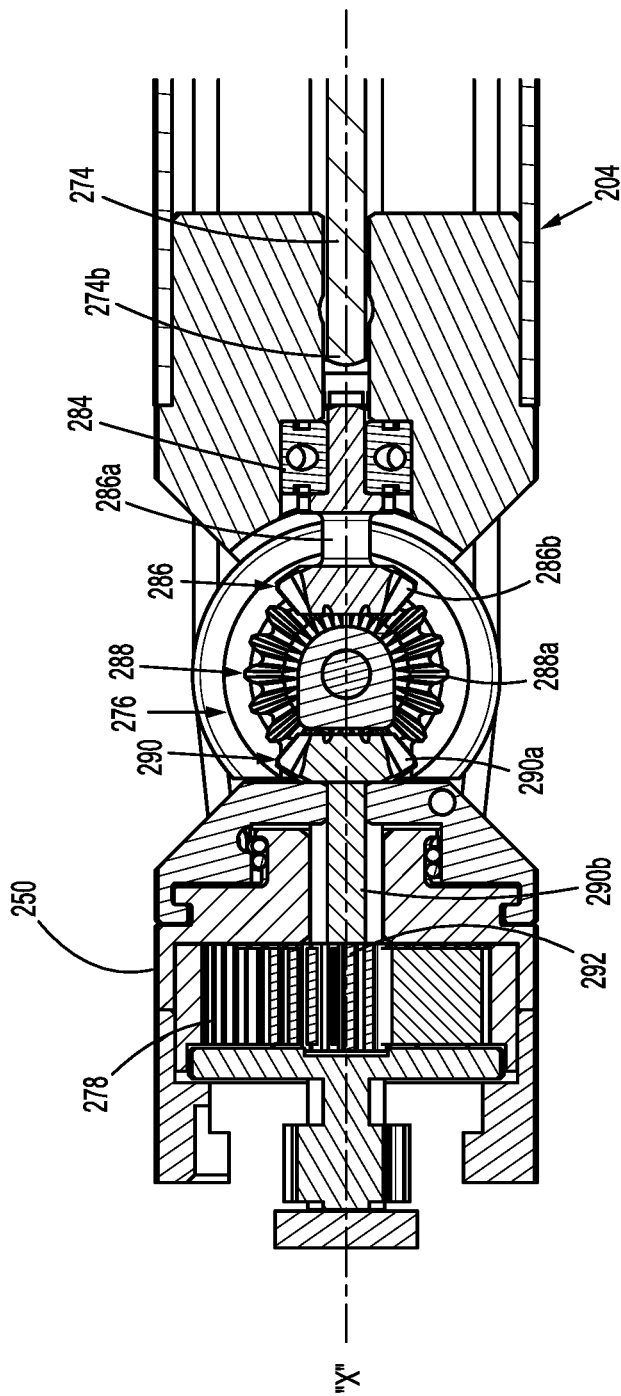
FIG. 13 is a cross-sectional view of the adapter assembly of FIGS. 1-6, taken along line 13-13 of FIG. 6.
Figure 16:
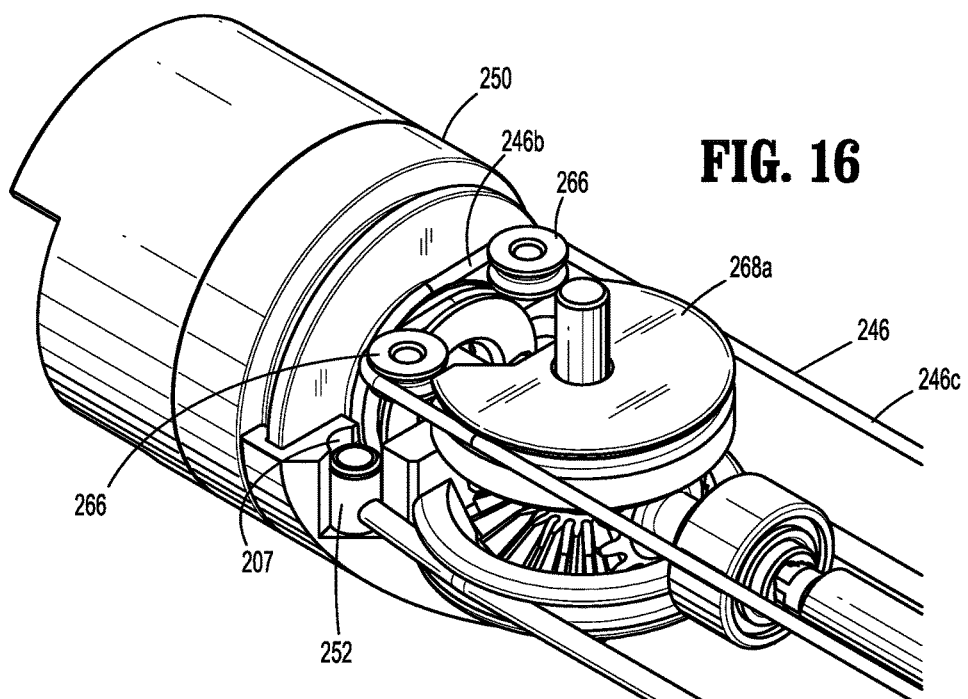
FIG. 16 is a perspective view, with parts removed, of a distal end portion of the adapter assembly of FIGS. 1-7 and 11-15.
Figure 17:
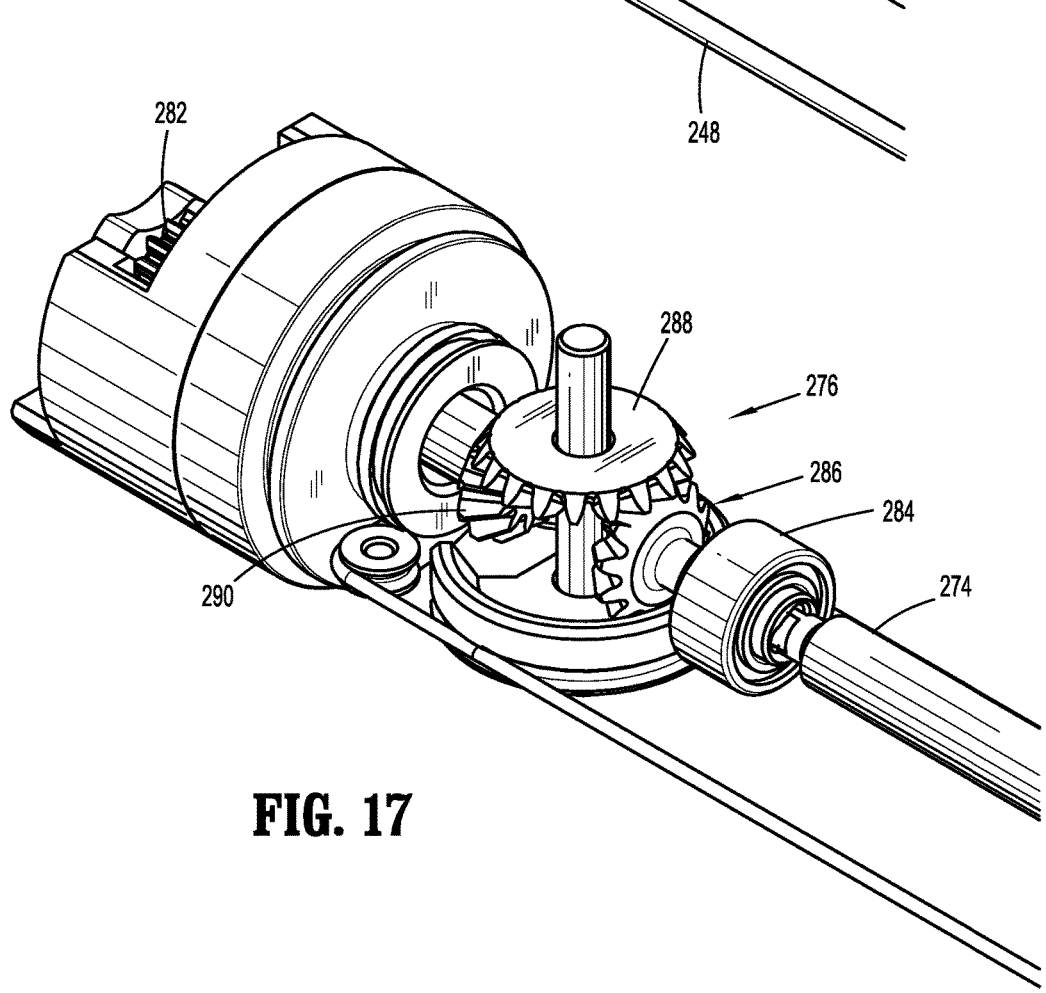
FIG. 17 is another perspective view, with parts removed, of the distal end portion of the adapter assembly of FIGS. 1-7 and 11-15.
Figure 18:
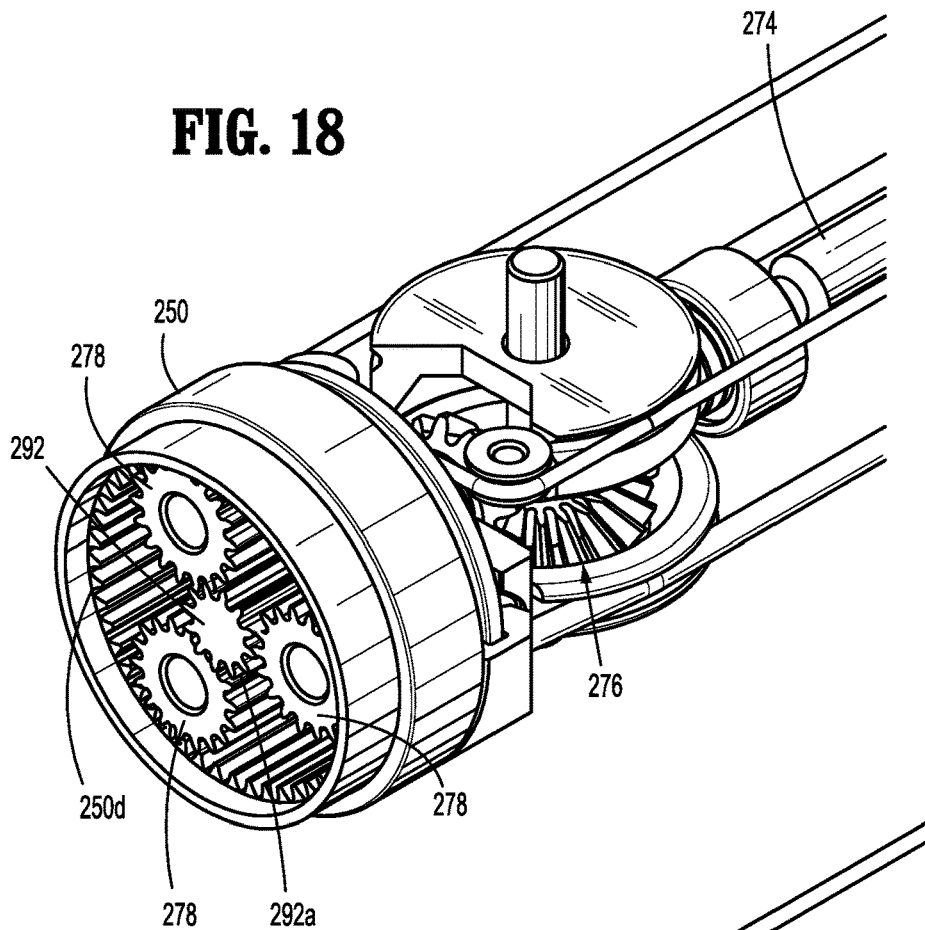
FIG. 18 is yet another perspective view, with parts removed, of the distal end portion of the adapter assembly of FIGS. 1-7 and 11-15.
Figure 19:
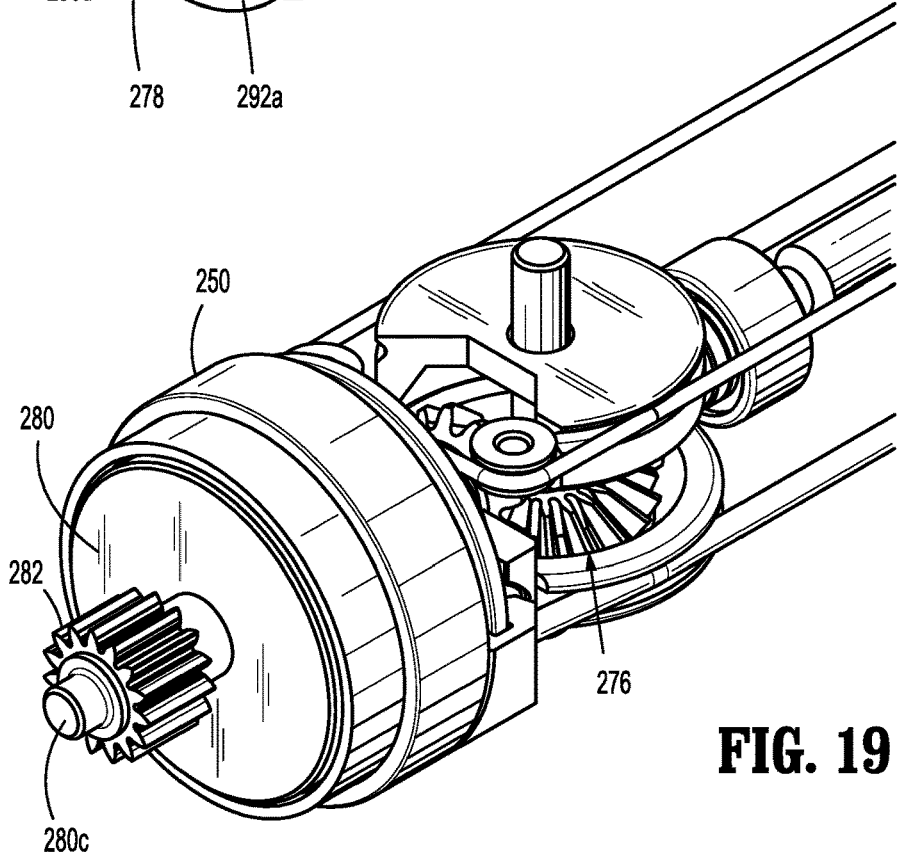
FIG. 19 is another perspective view, with parts removed, of the distal end portion of the adapter assembly of FIGS. 1-7 and 11-15.

As shown in FIGS. 4 and 12, a distalmost end of shaft 280c of spider plate 280 extends into opening 236a defined in tongue 236 of fourth segment 206d of distal end portion 206 of outer tube 204. Tongue 236 supports distal gear 282 so that teeth 282a of distal gear 282 are positioned between the pair of arms 230a and 230b of fourth segment 206d of distal end portion 206 of outer tube 204.

Figure 20:
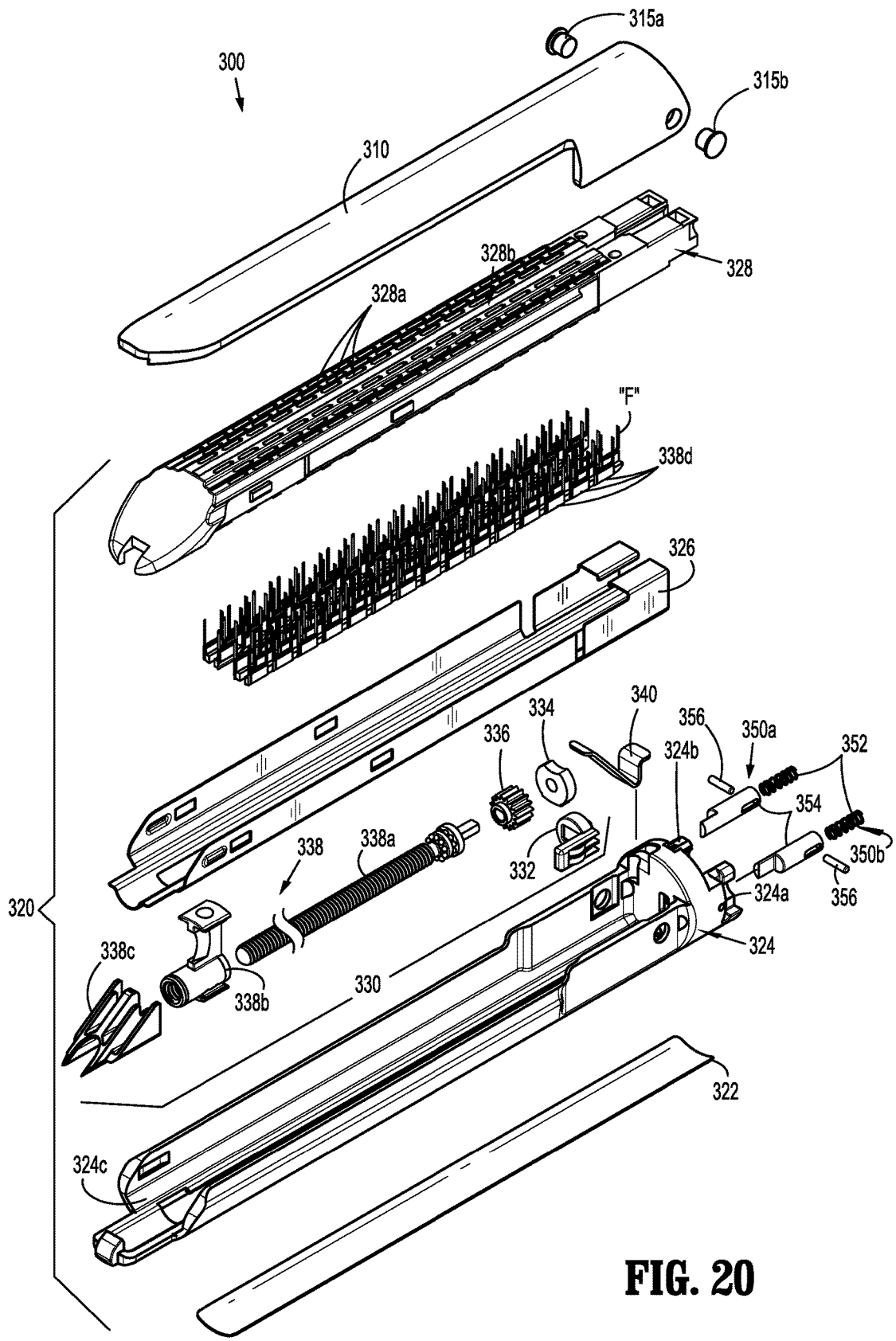
FIG. 20 is an enlarged, perspective view, with parts separated, of a surgical loading unit of the electromechanical surgical system of FIG. 1.

Turning now to FIG. 20, an embodiment of a surgical loading unit 300 is shown. Loading unit 300 includes anvil 310 and cartridge assembly 320 that are pinned together by a pair of pins 315a, 315b and movable between open and closed conditions. Anvil 310 and cartridge assembly 320 cooperate to apply a plurality of linear rows of fasteners "F" (e.g., staples). In certain embodiments, the fasteners are of various sizes, and, in certain embodiments, the fasteners are loaded into various lengths or rows of cartridge assembly 320, e.g., about 30, 45 and 60 mm in length.

Cartridge assembly 320 includes a base 322 secured to a mounting portion 324, a frame portion 326, and a cartridge portion 328 defining a plurality of fastener retaining slots 328a and a knife slot 328b in a tissue engaging surface thereof. Mounting portion 324 has mating surfaces 324a, 324b on a proximal end thereof and defines a receiving channel 324c therein that supports frame portion 326, cartridge portion 328, and a fastener firing assembly 330 therein. Cartridge assembly 320 supports a biasing member 340 that engages anvil 310.

Fastener firing assembly 330 includes an electrical contact member 332, such as a slip ring, among other known electrical connectors within the purview of those skilled in the art, for electrical communication with adapter assembly 200, which in turn, is configured for electrical connection with the circuit board (not shown) of surgical device 100 (FIG. 1). The fastener firing assembly further includes a bearing member 334, a gear member 336 that engages distal gear 282 of distal end portion 206 of outer tube 204, and a screw assembly 338. Screw assembly 338 includes a lead screw 338a, a drive beam 338b, and an actuation sled 338c that is engageable with a plurality of pusher members 338d.

Cartridge assembly 320 also supports a pair of plunger assemblies 350a, 350b. Each of the pair of plunger assemblies 350a, 350b includes a spring 352, a plunger 354, and a pin 356 that secures each plunger assembly to mounting portion 324. Plunger assemblies 350a, 350b cooperate with the proximal end of cartridge portion 328 to facilitate securement of cartridge portion 328 within mounting portion 324.

In order to secure the proximal end of loading unit 300 to distal end portion 206 of outer tube 204 of adapter assembly 200, the proximal end of loading unit 300 is aligned with distal end portion 206 of outer tube 204 so that the proximal end of loading unit 300 can be snapped together with distal end portion 206, as shown in FIG. 1, such that mating surfaces 324a and 324b of loading unit 300 engage with the pair of arms 230a and 230b of fourth segment 206d of distal end portion 206 so that the teeth of gear member 336 of loading unit 300 enmesh with the teeth 282a of distal gear 282 of adapter assembly 200.

To fire the plurality of fasteners "F," actuation pad 108 of device 100 is actuated to rotate rotatable drive shaft 106b (due to an actuation of a motor (not shown) within the handle housing 102), and to effectuate rotation of input socket 242b and firing shaft 274 of adapter assembly 200 about longitudinal axis "X". Rotation of firing shaft 274 rotates proximal bevel gear 286, which in turn, causes rotation of central bevel gear 288 and distal bevel gear 290. Rotation of distal bevel gear 290 causes a corresponding rotation of sun gear 292, which in turn, rotates the plurality of planetary gears 278 within ring gear 250. Rotation of the plurality of planetary gears 278 causes a corresponding rotation of spider plate 280 and thus distal gear 282. Rotation of distal gear 282 rotates lead screw 338a of loading unit 300 and enables drive beam 338a to axially advance along lead screw 338a and through longitudinal knife slot 328b by virtue of the threaded engagement between lead screw 338a and drive beam 338a. Drive beam 338a engages anvil 310 to maintain anvil 310 and cartridge assembly 320 in approximation. Distal advancement of drive beam 338b advances actuation sled 338c into engagement with the plurality of pusher members 328 and fires the plurality of fasteners "F" from the plurality of fastener retention slots 328a for forming against corresponding fastener forming pockets defined within anvil 310. Loading unit 300 can be reset and fastener cartridge 328 can be replaced so that loading unit 300 can then be re-fired as desired.

Figure 11:
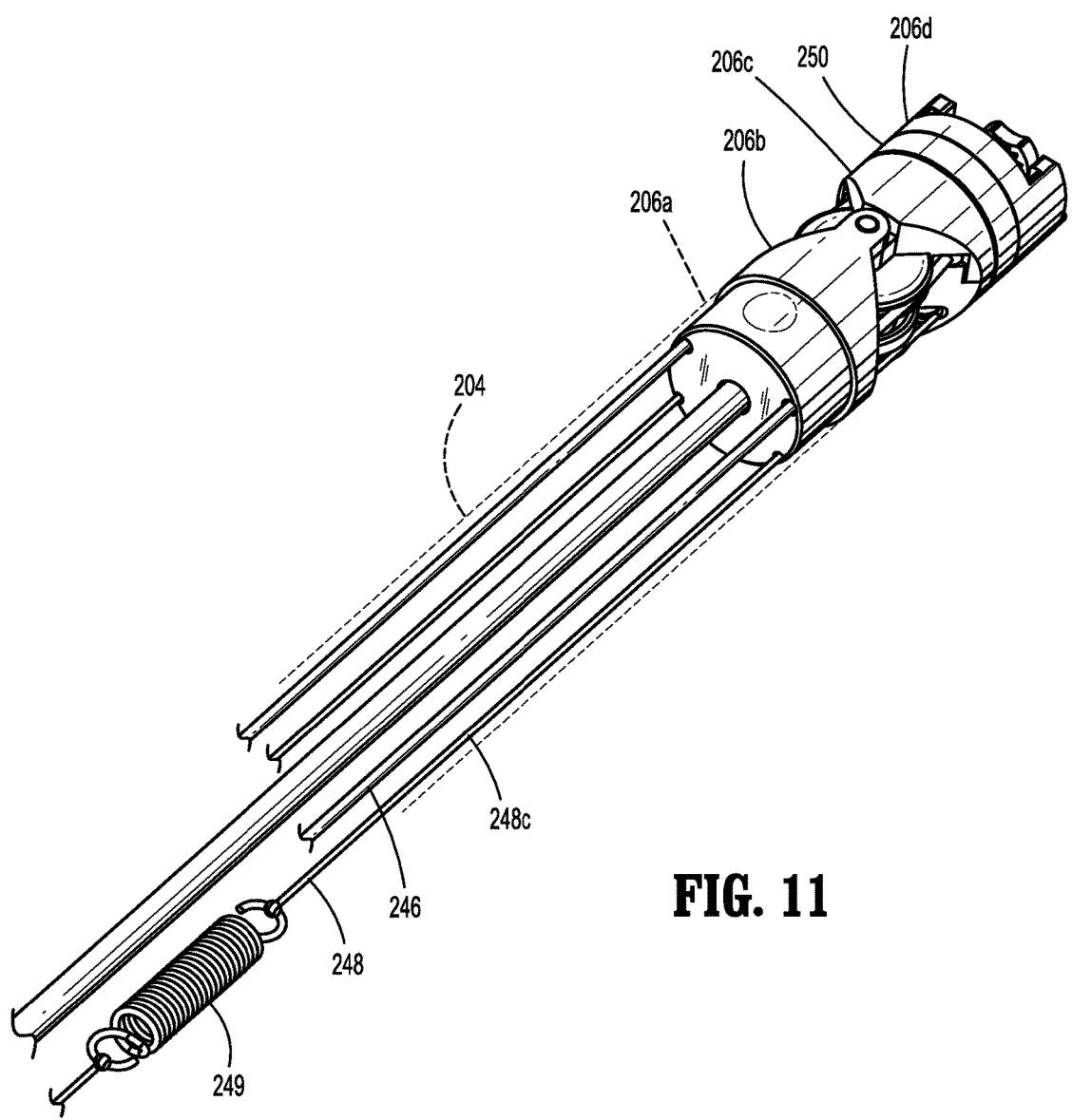
FIG. 11 is a perspective view, with parts removed, of internal components of an outer tube of the adapter assembly of FIGS. 1-7.
Figure 21:
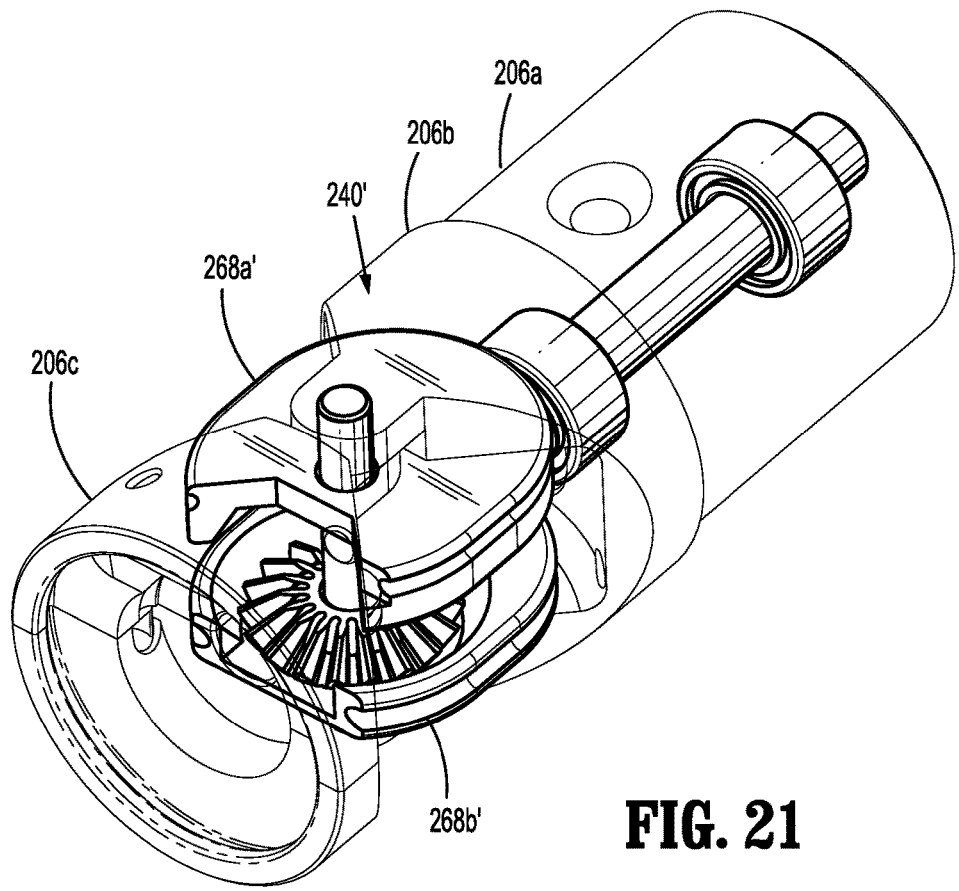
FIG. 21 is a perspective view, with parts removed, of a distal end portion of an adapter assembly in accordance with another embodiment of the present disclosure.
Figure 22:
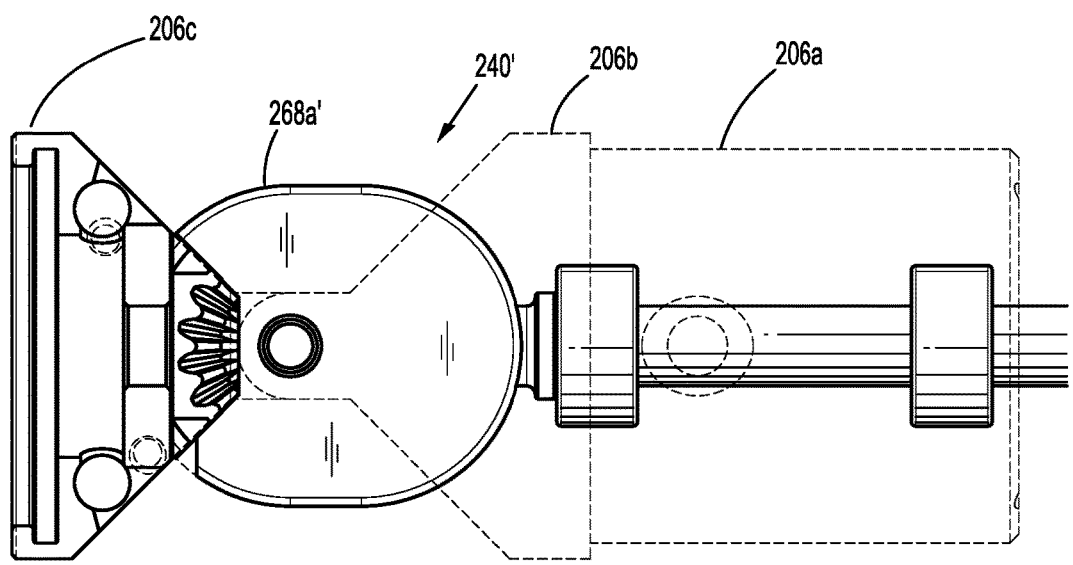
FIG. 22 is a top view of the distal end portion of the adapter assembly of FIG. 21.

Turning now to FIGS. 21 and 22, an articulation assembly 240' in accordance with another embodiment of the present disclosure, for adapter assembly 200, is shown. Articulation assembly 240' is substantially similar to articulation assembly 240 and thus, is only described herein to the extent necessary to describe the differences in construction and operation thereof. Articulation assembly 240' includes first and second cable guide wheels 268a' and 268b' that are cam-shaped. This shape compensates for changes in the tension/slack during articulation of the articulation cable (not shown), and thus, the articulation cable of this embodiment does not include springs 249 of articulation cable 248 (FIG. 11).

Figure 23:
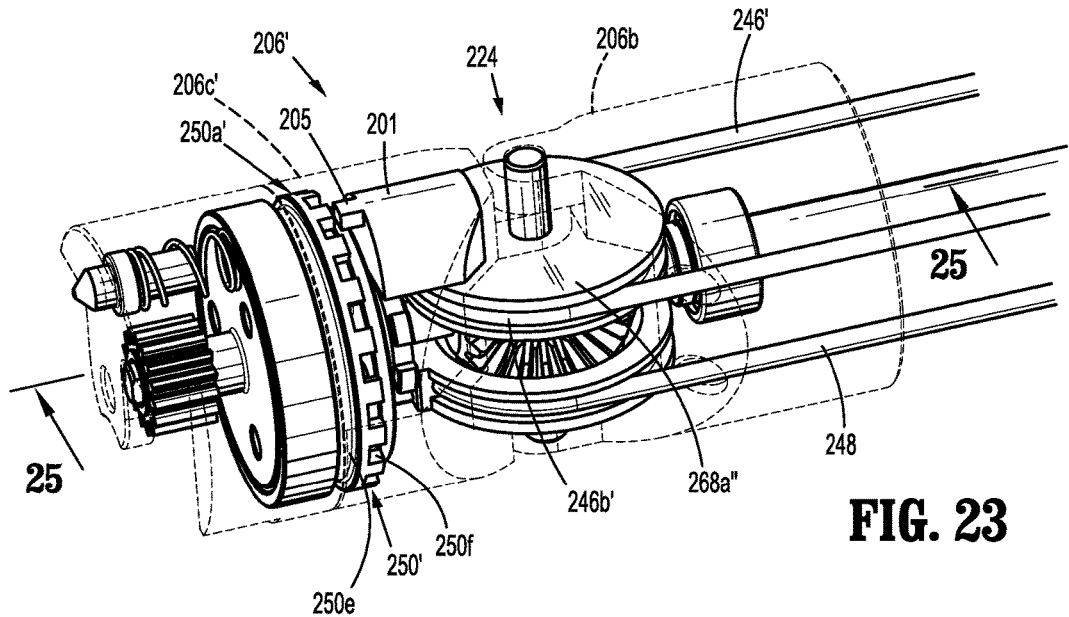
FIG. 23 is a perspective view, with parts removed, of a distal end portion of an adapter assembly in accordance with another embodiment of the present disclosure.
Figure 24:
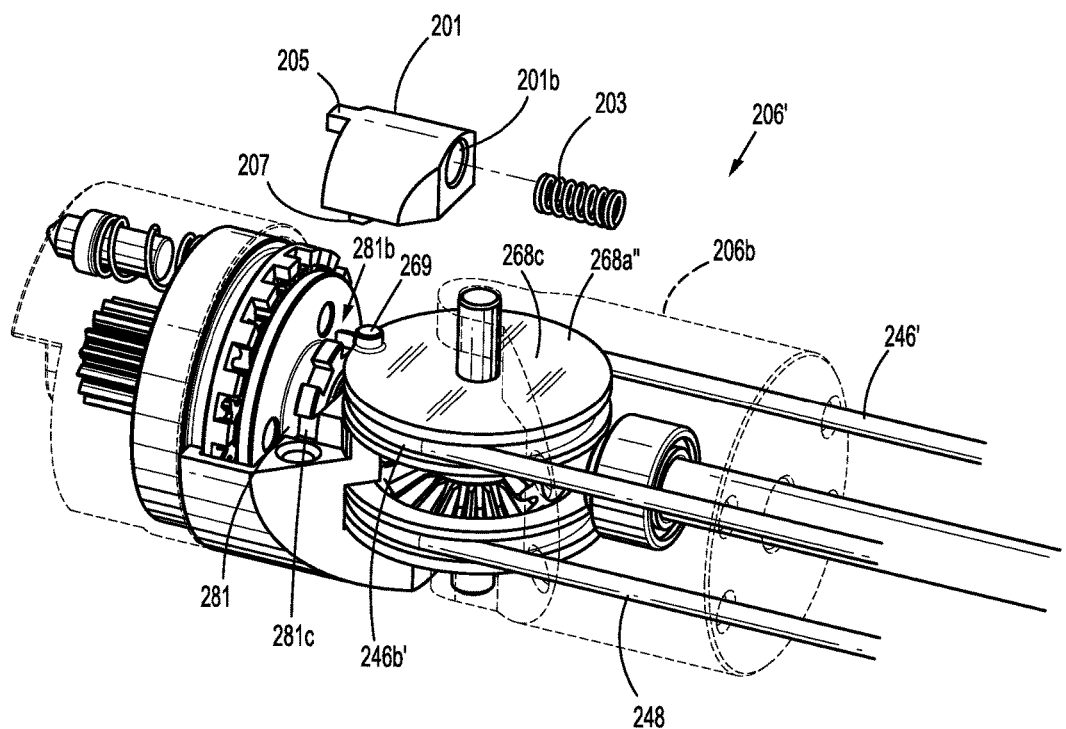
FIG. 24 is another perspective view, with parts removed, of the distal end portion of the adapter assembly of FIG. 23.
Figure 25:
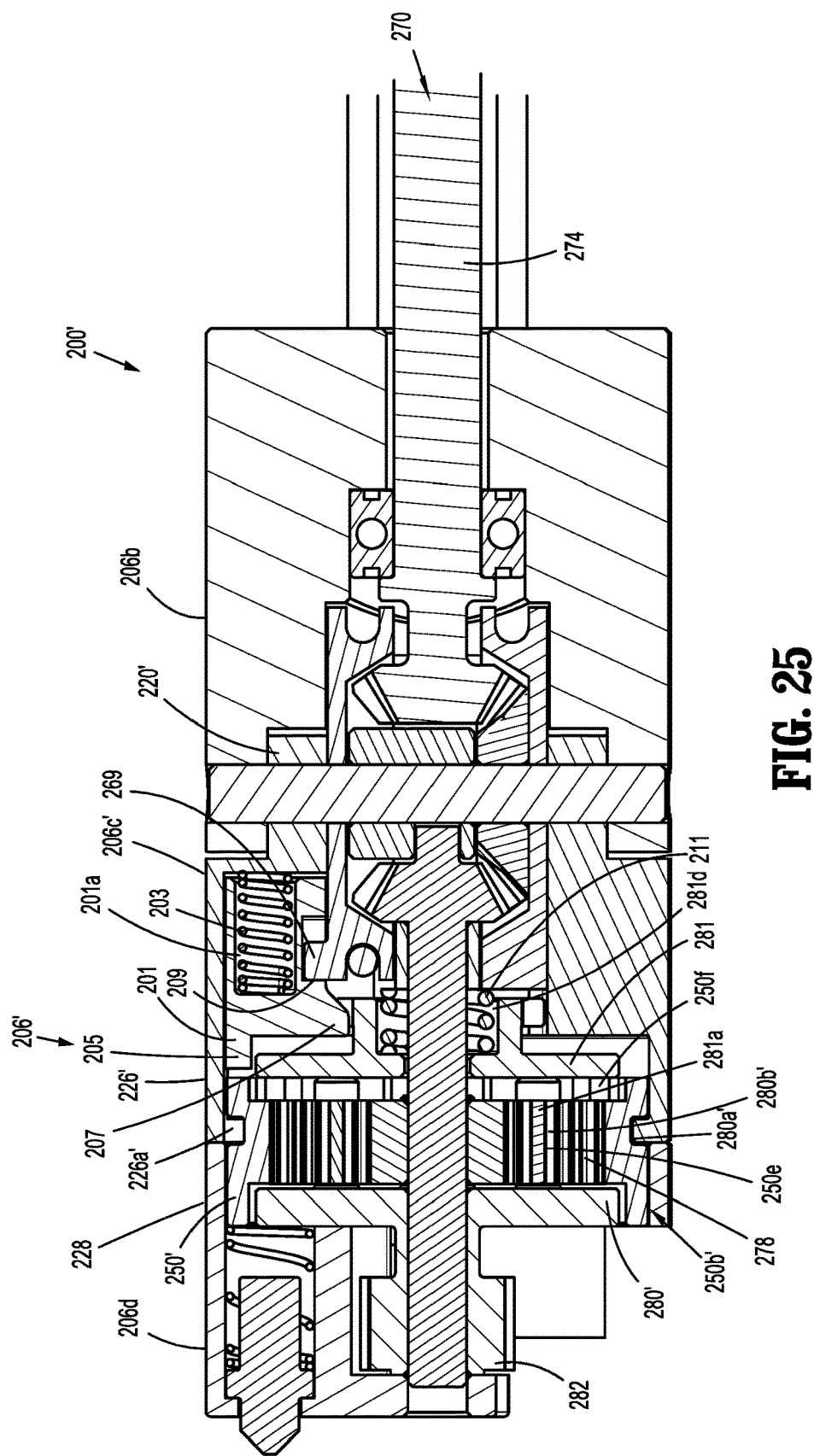
FIG. 25 is a cross-sectional view of the distal end portion of the adapter assembly of FIGS. 23 and 24.

Referring now to FIGS. 23-25, an adapter assembly 200' in accordance with another embodiment of the present disclosure is shown. Adapter assembly 200' is substantially similar to adapter assembly 200 and thus, is only described herein to the extent necessary to describe the differences in construction and operation thereof.

Adapter assembly 200' includes a distal end portion 206' having a third segment 206c' that forms an articulation joint 224 with second segment 206b. A switch 201 is disposed between proximal and distal ends 220' and 226' of third segment 206c'. Switch 201 includes a spring 203 supported within a cavity 201a defined within switch 201 and extending through an opening 201b disposed at a proximal end of switch 201. Spring 203 contacts an inner surface of third segment 206c' and is sufficiently compressible to enable switch 201 to be moved proximally and distally within third segment 206c' between a proximal position and a distal position. A tab 205 extends distally from a distal end of switch 201, and an extension 207 extends inwardly from a bottom surface of switch 201 towards a center of outer tube 204'. Distal end 226' of third segment 206c' includes a cylindrical lip 226a' that mounts over and catches a recess 250e defined within an outer surface of ring gear 250'. Distal end 226' of third segment 206c' abuts a proximal end 228 of fourth segment 206d which is fixedly secured to ring gear 250'.

Ring gear 250' includes a proximal end 250a' having a plurality of recesses 250f radially disposed therearound. Recesses 250f are dimensioned to receive and engage tab 205 of switch 201 when switch 201 is moved to the distal position. Spring 203 applies a distal force on switch 201 until tab 205 of switch 201 is aligned with, and engages, one of the recesses 250f of ring gear 250'.

Spider plate 280' (FIG. 25) is disposed within a distal end 250b' of ring gear 250' and is operably coupled to the plurality of planetary gears 278 via pegs 280b (FIG. 7), as described above with regard to spider plate 280'. A spider gear 281 is disposed proximal of ring gear 250' and is operably coupled to spider plate 280'. In embodiments, spider gear 281 includes a plurality of pegs 281a extending distally therefrom that are press fit into openings 280a' defined in bosses 280b' extending proximally from the spider plate 280'. Spider gear 281 includes a proximal end 281b having a plurality of recesses 281c disposed radially therearound. Recesses 281c are dimensioned to engage extension 207 of switch 201 when switch 201 is moved to the proximal position. A spring 211 is supported within a cavity 281d defined in the spider gear 281 and applies a force on the spider gear 281 to aid in alignment of one of the recesses 281c of the spider gear 281 with the extension 207 of the switch 201.

Adapter assembly 200' includes a pull cable 246' having a proximal end portion (not shown) wound around drum surface 264a of drum portion 264 of worm wheel 260 of the first worm drive 254 (see e.g., FIG. 9), and a distal end portion 246b' wraps around a first cable guide wheel 268a". First cable guide wheel 268a" includes a cam 269 extending from a top surface 268c thereof that engages a camming surface 209 of switch 201. Cam 269 is movable between a distal position and a proximal position. In the distal position, cam 269 contacts camming surface 209 of switch 201 and moves switch 201 distally such that tab 205 of switch 201 is received within one of the recesses 250f of ring gear 250', and extension 207 of switch 201 is moved distal to, and out of engagement with, one of the recesses 281c of spider gear 281. In the proximal position, cam 269 releases camming surface 207 of switch 201 and switch 201 moves proximally such that tab 205 of switch 201 is not engaged with ring gear 250', and extension 207 of switch 201 is received within one of the recesses 281c of spider gear 281.

In use, rotation of first cable guide wheel 268a' causes cam 269 to move proximally or distally, which in turn, moves switch 201 proximally or distally within third segment 206c' of distal portion 206'. In the distal position, tab 205 is engaged with one of the recesses 250f of ring gear 250' and thus holds ring gear 250' stationary, and extension 207 is disengaged from one of the recesses 281c of spider gear 281 thereby allowing for the plurality of planetary gears 278 to turn spider plate 280' during firing of firing assembly 270, which in turn, allows rotation of distal gear 282 for effecting a function of loading unit 300. In the proximal position, tab 205 is disengaged from ring gear 250' and extension 207 is engaged with one of the recesses 281c of spider gear 281 such that the spider gear 281, and thus spider plate 280, are held stationary, allowing the plurality of planetary gears 278 to rotate ring gear 250' during actuation of firing shaft 274, thereby rotating distal end portion 206' of outer tube 204', and thus loading unit 300.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An adapter assembly for selectively interconnecting a surgical loading unit that is configured to perform a function and a surgical device that is configured to actuate the surgical loading unit, the surgical loading unit including an axially translatable drive member, and the surgical device including a plurality of rotatable drive shafts, the adapter assembly comprising:
   a housing configured and adapted for connection with the surgical device;
   an outer tube extending distally from the housing to a distal end portion configured and adapted for connection with the surgical loading unit, the distal end portion of the outer tube including a switch having a tab extending distally from a distal end of the switch and an extension extending inwardly toward a center of the outer tube; and
   a firing assembly supported within the housing and the outer tube, the firing assembly including:
      a firing shaft including a proximal end configured for operative engagement with a rotatable drive shaft of the plurality of rotatable drive shafts of the surgical device;
      a bevel gear assembly including a proximal end in mechanical engagement with a distal end portion of the firing shaft;
      a ring gear disposed within the distal end portion of the outer tube;
      a sun gear disposed at a distal end of the bevel gear assembly within the ring gear;
      a plurality of planetary gears disposed around and meshingly engaged with teeth of the sun gear and teeth of the ring gear;
      a spider plate operably coupled to the plurality of planetary gears;
      a spider gear operably coupled to the spider plate and disposed proximal of the ring gear; and
      a distal gear disposed on a shaft extending distally from the spider plate, the distal gear being operatively engageable with the axially translatable drive member of the surgical loading unit,
   the switch being movable between a proximal position in which the tab is disengaged from the ring gear and the extension is engaged with the spider gear such that the spider plate is held stationary to allow the plurality of planetary gears to rotate the distal end portion of the outer tube, and a distal position in which the tab is engaged with the ring gear and the extension is disengaged from the spider gear such that the ring gear is held stationary to allow the plurality of planetary gears to effect a function of the surgical loading unit.

2. The adapter assembly of claim 1, wherein the distal end portion of the outer tube includes an articulation joint.

3. The adapter assembly of claim 2, wherein the bevel gear assembly is disposed proximal of the articulation joint.

4. The adapter assembly of claim 3, wherein the sun gear and the plurality of planetary gears are disposed distal of the articulation joint.

5. The adapter assembly of claim 1, wherein the bevel gear assembly includes a proximal bevel gear including a stem extending proximally therefrom that is operably coupled to a distal end portion of the firing shaft by a bearing.

6. The adapter assembly of claim 5, wherein the bevel gear assembly further includes a central bevel gear engaged with the proximal bevel gear.

7. The adapter assembly of claim 6, wherein the bevel gear assembly further includes a distal bevel gear engaged with the central bevel gear.

8. The adapter assembly of claim 7, wherein the distal bevel gear of the bevel gear assembly includes a stem extending distally therefrom, and the sun gear is secured to the stem of the distal bevel gear.

9. The adapter assembly of claim 1, wherein the spider plate includes a proximal surface including a plurality of pegs extending proximally therefrom that are disposed in openings defined in the plurality of planetary gears.

10. An adapter assembly for selectively interconnecting a surgical loading unit that is configured to perform a function and a surgical device that is configured to actuate the surgical loading unit, the surgical loading unit including an axially translatable drive member, and the surgical device including a plurality of rotatable drive shafts, the adapter assembly comprising:
   a housing configured and adapted for connection with the surgical device;
   an outer tube extending distally from the housing to a distal end portion configured and adapted for connection with the surgical loading unit, the distal end portion of the outer tube including an articulation joint;
   a firing assembly supported within the housing and the outer tube, the firing assembly including:
      a firing shaft including a proximal end configured for operative engagement with a rotatable drive shaft of the plurality of rotatable drive shafts of the surgical device;
      a bevel gear assembly including a proximal end in mechanical engagement with a distal end portion of the firing shaft;
      a ring gear disposed within the distal end portion of the outer tube;
      a sun gear disposed at a distal end of the bevel gear assembly within the ring gear;
      a plurality of planetary gears disposed around and meshingly engaged with teeth of the sun gear and teeth of the ring gear;
      a spider plate operably coupled to the plurality of planetary gears; and
      a distal gear disposed on a shaft extending distally from the spider plate, the distal gear being operatively engageable with the axially translatable drive member of the surgical loading unit; and
   an articulation assembly including:
      a worm gear assembly including a first worm drive and a second worm drive disposed within the housing;
      a rotation cable operably connected to and extending distally from the first worm drive of the worm gear assembly through the outer tube to the ring gear which is disposed distal to the articulation joint such that rotation of the first worm drive results in rotation of the distal end portion of the outer tube; and an articulation cable operably connected to and extending distally from the second worm drive of the worm gear assembly to retaining members disposed within the outer tube distal to the articulation joint such that rotation of the second worm drive results in articulation of the distal end portion of the outer tube about the articulation joint.

11. The adapter assembly of claim 10, wherein each of the first and second worm drives including a worm screw meshingly engaged with a worm wheel, each worm screw configured to be in operative communication with a rotatable drive shaft of the plurality of drive shafts of the surgical device.

12. The adapter assembly of claim 11, wherein the rotation cable includes a proximal end wound around a drum portion of the worm wheel of the first worm drive and a distal end wound around a drum of the ring gear.

13. The adapter assembly of claim 11, wherein the articulation cable includes a proximal end wound around a drum portion of the worm wheel of the second worm drive and distal ends coupled to respective retaining members.

14. The adapter assembly of claim 13, further comprising springs disposed between the proximal and distal ends of the articulation cable.

15. The adapter assembly of claim 11, wherein the articulation assembly further includes a first cable guide wheel and a second cable guide wheel for guiding the rotation and articulation cables, respectively.

16. The adapter assembly of claim 15, wherein the first and second cable guide wheels are circular in shape.

17. The adapter assembly of claim 15, wherein the first and second guide wheels are cam-shaped.

18. The adapter assembly of claim 2, further comprising an articulation assembly including:
a worm gear assembly including a first worm drive and a second worm drive disposed within the housing;
a pull cable operably connected to and extending distally from the first worm drive of the worm gear assembly and into the outer tube, the pull cable configured to move the switch between the proximal and distal positions; and
an articulation cable operably connected to and extending distally from the second worm drive of the worm gear assembly to retaining members disposed within the outer tube distal of the articulation joint such that rotation of the second worm drive results in articulation of the distal end portion of the outer tube about the articulation joint.

19. The adapter assembly of claim 18, wherein the articulation assembly further includes a first cable guide wheel including a cam, and the pull cable includes a proximal end wound around a drum portion of the worm wheel of the first worm drive of the worm gear assembly and a distal end wrapped around the first cable guide wheel such that rotation of the first worm drive results in movement of the cam against a camming surface of the switch to move the switch between the proximal and distal positions.

* * * * *